US012699089B2

(12) United States Patent
Ando

(10) Patent No.: US 12,699,089 B2
(45) Date of Patent: Aug. 4, 2026

(54) BACTERIOLYSIS METHOD, BACTERIOLYSIS AID, AND METHOD FOR DETERMINING THE PRESENCE OR ABSENCE OF BACTERIA

(71) Applicant: ASAHI KASEI KABUSHIKI KAISHA, Tokyo (JP)

(72) Inventor: Yu Ando, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 270 days.

(21) Appl. No.: 18/693,477

(22) PCT Filed: Nov. 24, 2023

(86) PCT No.: PCT/JP2023/042246
§ 371 (c)(1),
(2) Date: Mar. 19, 2024

(87) PCT Pub. No.: WO2024/111665
PCT Pub. Date: May 30, 2024

(65) Prior Publication Data
US 2025/0138008 A1 May 1, 2025

(30) Foreign Application Priority Data
Nov. 24, 2022 (JP) ................................ 2022-187691

(51) Int. Cl.
*G01N 33/569* (2006.01)
*C12N 1/06* (2026.01)
*C12N 9/36* (2006.01)
*C12N 9/64* (2006.01)
*C12Q 1/37* (2006.01)

(52) U.S. Cl.
CPC ......... *G01N 33/56938* (2013.01); *C12N 1/06* (2013.01); *C12N 9/2462* (2013.01); *C12N 9/6489* (2013.01); *C12Q 1/37* (2013.01); *C12Y 302/01017* (2013.01); *C12Y 302/01052* (2013.01); *C12Y 304/24075* (2013.01)

(58) Field of Classification Search
None
See application file for complete search history.

(56) References Cited

U.S. PATENT DOCUMENTS

| | | | |
|---|---|---|---|
| 2015/0160212 | A1 | 6/2015 | Maehana et al. |
| 2016/0313327 | A1 | 10/2016 | Maehana et al. |
| 2016/0313328 | A1 | 10/2016 | Utsumi et al. |
| 2016/0320387 | A1 | 11/2016 | Maehana et al. |
| 2022/0042990 | A1 | 2/2022 | Maehana |
| 2022/0227805 | A1 | 7/2022 | Means et al. |

FOREIGN PATENT DOCUMENTS

| | | | |
|---|---|---|---|
| EP | 4 317 183 | A1 | 2/2024 |
| JP | 2009-263296 | A | 11/2009 |
| JP | 2017-32579 | A | 2/2017 |
| WO | WO 2013/186885 | A1 | 12/2013 |
| WO | WO 2015/093544 | A1 | 6/2015 |
| WO | WO 2015/093545 | A1 | 6/2015 |
| WO | WO 2015/093546 | A1 | 6/2015 |
| WO | WO 2020/111223 | A1 | 6/2020 |
| WO | WO 2022/210594 | A1 | 10/2022 |
| WO | WO 2023/095845 | A1 | 6/2023 |

OTHER PUBLICATIONS

Jagielska et al., "LytM Fusion with SH3b-Like Domain Expands Its Activity to Physiological Conditions," Microbial Drug Resistance, vol. 22, No. 6, 2016, pp. 461-469.
Yoshimura et al., "Identification and Molecular Characterization of N-Acetylmuraminidase, Aml, Involved in *Steptococcus mutans* Cell Separation," Microbial. Immunol., vol. 50, No. 9, 2006, pp. 729-742.
International Preliminary Report on Patentability and Written Opinion of the International Searching Authority for International Application No. PCT/JP2023/042246, dated May 27, 2025, with an English translation.
International Search Report for International Application No. PCT/JP2023/042246, dated Feb. 6, 2024, with an English translation.
Supplementary European Search Report for European Application No. 23864108.8, dated Mar. 11, 2026.
Kiku et al., "Evaluation of a rapid coliform detection kit from clinical mastitis milk using colloidal gold nanoparticle-based immunochromatographic strips," The Journal of Veterinary Medical Science, vol. 83, No. 11, Sep. 15, 2021, pp. 1628-1633.

*Primary Examiner* — Oluwatosin A Ogunbiyi
(74) *Attorney, Agent, or Firm* — Birch, Stewart, Kolasch & Birch, LLP

(57) ABSTRACT

A method for lysing a group of bacteria in the sample, comprising the step of lysing the group of bacteria in the sample in a mixture solution obtained by mixing the sample, a bacteriolysis enzyme, and a bacteriolysis aid, wherein the bacteriolysis enzyme includes at least one bacteriolysis enzyme selected from the group consisting of lysostaphin, lysozyme, acetyl glucosaminidase, and endopeptidase, and wherein the mixture solution has a pH of from 6.0 to 7.0 and an electrical conductivity of from 2.5 to 8.5 mS/cm, whereby bacteriolysis of two or more species of bacteria becomes possible.

39 Claims, 5 Drawing Sheets

BACTERIOLYSIS METHOD, BACTERIOLYSIS AID, AND METHOD FOR DETERMINING THE PRESENCE OR ABSENCE OF BACTERIA

TECHNICAL FIELD

The present invention relates to a method for lysing two or more species of bacteria in a sample. The present invention also relates to a bacteriolysis aid for use in the bacteriolysis method according to the present invention, a bacteriolysis kit containing the bacteriolysis aid, a bacterial detection kit for use in the bacterial detection method, and a method for determining the presence or absence of bacteria.

BACKGROUND ART

Conventionally, various techniques have been used to lyse bacteria in samples in order to detect bacteria based on their intracellular components. For example, Patent Literatures 1 and 2 describe methods for detecting *Staphylococcus aureus* based on its ribosome protein L7/L12 using an antigen-antibody reaction, in which methods lysostaphin is used as a lysing agent to lyse bacteria in the sample. Patent Literature 3 describes a method for detecting *E. coli* based on its ribosome protein L7/L12 using an antigen-antibody reaction, in which method lysozyme is used as a lysing agent to lyse bacteria in the sample. Patent Literature 4 discloses a technique for detecting a *Streptococcus* sp. in a sample based on an antigen-antibody reaction based on its ribosomal protein L7/L12, in which lysozyme and labiase are used as bacteriolytic enzymes to lyse bacteria in the sample.

LIST OF CITATIONS

Patent Literature

[Patent Literature 1] JP2017-032579 A
[Patent Literature 2] WO2015/093544 A
[Patent Literature 3] WO2015/093545 A
[Patent Literature 4] WO2015/093546 A

SUMMARY OF INVENTION

Problem to be Solved by the Invention

In conventional bacteriolysis methods such as those described in Patent Literatures 1 to 4, the conditions for maintaining the activity of each bacteriolytic enzyme are different. Therefore, when detecting bacteria of different lysis targets, it is necessary to perform lysis separately using lysis solutions containing the appropriate lysing enzyme for each target and optimized conditions for the lysing enzyme. This may lead to complicated and delayed bacteriolysis processing, and also may cause a mistake of using a wrong bacteriolysis solution for each bacteriolysis target.

Means to Solve the Problem

The present inventors have diligently studied the conditions for achieving bacteriolysis using at least one bacteriolysis enzyme selected from the group consisting of lysostaphin, lysozyme, acetyl glucosaminidase, and endopeptidase. As a result, the present inventors have found that adjusting the pH and the electrical conductivity of the reaction solution allows for all of the selected bacteriolysis enzymes to exhibit their activity and detect their respective target bacteria.

Specifically, some aspects of the present invention include the following.

[Aspect 1] A method for lysing a group of bacteria in the sample, comprising the step of lysing the group of bacteria in the sample in a mixture solution obtained by mixing the sample, a bacteriolysis enzyme, and a bacteriolysis aid, wherein the bacteriolysis enzyme includes at least one bacteriolysis enzyme selected from the group consisting of lysostaphin, lysozyme, acetyl glucosaminidase, and endopeptidase, and wherein the mixture solution has a pH of from 6.0 to 7.0 and an electrical conductivity of from 2.5 to 8.5 mS/cm.

[Aspect 2] The method according to Aspect 1, wherein the bacteriolysis enzyme and the bacteriolysis aid are premixed.

[Aspect 3] The method according to Aspect 1, wherein the bacteriolysis aid contains a buffer and a surfactant.

[Aspect 4] The method according to Aspect 3, wherein the bacteriolysis aid further contains a salt.

[Aspect 5] The method according to Aspect 3, wherein the surfactant contains at least nonionic surfactant.

[Aspect 6] The method according to Aspect 5, wherein the nonionic surfactant includes a first nonionic surfactant having a polyoxyethylene chain, wherein the polyoxyethylene chain has an average number of repeats of from 7 to 11 and an HLB value of 12.0 or more less than 14.5.

[Aspect 7] The method according to Aspect 6, wherein the polyoxyethylene chain has an average number of repeats of from 7.5 to 10 and an HLB value of 12.4 to 14.1.

[Aspect 8] The method according to Aspect 6, wherein the concentration of the first nonionic surfactant in the mixture solution is from 1.25 to 3.125%.

[Aspect 9] The method according to Aspect 5, wherein the bacteriolysis aid contains 5 to 500 mM buffer.

[Aspect 10] The method according to Aspect 1, wherein the bacteriolysis enzyme include all four bacteriolysis enzymes selected from the group consisting of lysostaphin, lysozyme, acetyl glucosaminidase, and endopeptidase.

[Aspect 11] The method according to Aspect 1, wherein the bacteriolysis subject of the method includes at least one bacterial species selected from the group consisting of *Escherichia* species, *Staphylococcus* species, and *Streptococcus* species.

[Aspect 12] The method according to Aspect 10, wherein the bacteriolysis subject of the method includes *Escherichia* species, *Staphylococcus* species, and *Streptococcus* species.

[Aspect 13] The method according to any one of Aspects 1 to 12, wherein the method is carried out as a pretreatment for L7/L12 ribosome protein antigen detection.

[Aspect 14] The method according to any one of Aspects 1 to 12, wherein the sample is milk.

[Aspect 15] A method for lysing a group of bacteria in a sample, comprising the step of mixing the sample, a bacteriolysis enzyme, and a bacteriolysis aid, wherein the bacteriolysis enzyme includes at least one bacteriolysis enzyme selected from the group consisting of lysostaphin, lysozyme, acetyl glucosaminidase, and endopeptidase, and wherein the bacteriolysis aid has a pH of from 6.0 to 7.0 and an electrical conductivity of from 2.0 to 8.0 mS/cm.

[Aspect 16] The method according to Aspect 15, wherein the bacteriolysis enzyme and the bacteriolysis aid are provided as a pre-mixed state.

[Aspect 17] The method according to Aspect 15, wherein the bacteriolysis aid contains a buffer and a surfactant.

[Aspect 18] The method according to Aspect 17, wherein the bacteriolysis aid further contains a salt.

[Aspect 19] The method according to Aspect 17, wherein the surfactant contains at least nonionic surfactant.

[Aspect 20] The method according to Aspect 19, wherein the nonionic surfactant includes a first nonionic surfactant having a polyoxyethylene chain, wherein the polyoxyethylene chain has an average number of repeats of from 7 to 11 and an HLB value of 12.0 or more less than 14.5.

[Aspect 21] The method according to Aspect 20, wherein the polyoxyethylene chain has an average number of repeats of from 7.5 to 10 and an HLB value of 12.4 to 14.1.

[Aspect 22] The method according to Aspect 19, wherein the concentration of the nonionic surfactant in the bacteriolysis aid is from 2 to 5%.

[Aspect 23] The method according to Aspect 17, wherein the bacteriolysis aid contains 5 to 500 mM buffer.

[Aspect 24] The method according to Aspect 15, wherein the bacteriolysis enzyme include all four bacteriolysis enzymes selected from the group consisting of lysostaphin, lysozyme, acetyl glucosaminidase, and endopeptidase.

[Aspect 25] The method according to Aspect 15, wherein the bacteriolysis subject of the method includes at least one bacterial species selected from the group consisting of *Escherichia* species, *Staphylococcus* species, and *Streptococcus* species.

[Aspect 26] The method according to Aspect 24, wherein the bacteriolysis subject of the method includes *Escherichia* species, *Staphylococcus* species, and *Streptococcus* species.

[Aspect 27] The method according to any one of Aspects 15 to 26, wherein the method is carried out as a pretreatment for L7/L12 ribosome protein antigen detection.

[Aspect 28] The method according to any one of Aspects 15 to 26, wherein the sample is milk.

[Aspect 29] The method according to any one of Aspects 15 to 26, wherein the sample and the bacteriolysis aid are mixed at a ratio of from 1:5 to 3:1.

[Aspect 30] A bacteriolysis aid comprising 0 to 1.5M of salts, 5 to 500 mM of a buffer, and 2 to 5% of a nonionic surfactant, and having a pH of from 6.0 to 7.0 and an electrical conductivity of from 2.0 to 8.0 mS/cm, in a sample in combination with at least one bacteriolysis enzyme selected from the group consisting of lysostaphin, lysozyme, acetyl glucosaminidase, and endopeptidase for lysing a group of bacteria including *Escherichia* species, *Staphylococcus* species, and *Streptococcus* species.

[Aspect 31] A bacteriolysis kit comprising at least one bacteriolysis enzyme selected from the group consisting of lysostaphin, lysozyme, acetyl glucosaminidase, and endopeptidase and the bacteriolysis aid according to Aspect 30.

[Aspect 32] A bacterial detection kit comprising at least one bacteriolysis enzyme selected from the group consisting of lysostaphin, lysozyme, acetyl glucosaminidase, and endopeptidase, the bacteriolysis aid according to Aspect 30, and a device for detecting a L7/L12 ribosome protein antigen.

[Aspect 33] A method for determining the presence or absence of at least one species of bacteria selected from the group consisting of *Escherichia* species, *Staphylococcus* species, and *Streptococcus* species in a sample, comprising the steps of:

mixing the sample, a bacteriolysis enzyme, and a bacteriolysis aid to prepare a mixture solution; and determining the presence or absence of the bacteria by detecting a L7/L12 ribosome protein derived from the bacteria contained in the mixture solution by means of an immunological method, wherein the bacteriolysis enzyme includes at least one bacteriolysis enzyme selected from the group consisting of lysostaphin, lysozyme, acetyl glucosaminidase, and endopeptidase, wherein the mixture solution has a pH of from 6.0 to 7.0 and an electrical conductivity of from 2.5 to 8.5 mS/cm, wherein in the step to prepare the mixture solution, the lysozyme can lyse the *Escherichia* species, the lysostaphin can lyse the *Staphylococcus* species, and the lysozyme, acetyl glucosaminidase, and endopeptidase can lyse the *Streptococcus* species.

[Aspect 34] The method according to Aspect 33, wherein the bacteriolysis aid contains a buffer and a surfactant.

[Aspect 35] The method according to Aspect 34, wherein the surfactant contains at least nonionic surfactant.

[Aspect 36] The method according to Aspect 35, wherein the nonionic surfactant includes a first nonionic surfactant having a polyoxyethylene chain, wherein the polyoxyethylene chain has an average number of repeats of from 7 to 11 and an HLB value of 12.0 or more less than 14.5.

[Aspect 37] The method according to Aspect 36, wherein the polyoxyethylene chain has an average number of repeats of from 7.5 to 10 and an HLB value of 12.4 to 14.1.

[Aspect 38] The method according to Aspect 36, wherein the concentration of the first nonionic surfactant in the mixture solution is from 1.25 to 3.125%.

[Aspect 39] The method according to Aspect 33, wherein the bacteriolysis enzyme include all four bacteriolysis enzymes selected from the group consisting of lysostaphin, lysozyme, acetyl glucosaminidase, and endopeptidase.

[Aspect 40] The method according to Aspect 39, wherein in the step, the bacteriolysis enzyme can lyse all of the *Escherichia* species, the *Staphylococcus* species, and the *Streptococcus* species.

Effect of the Invention

According to the present invention, bacteriolysis with different bacteriolysis enzymes can be achieved using the same bacteriolysis aid. This eliminates the need to select an appropriate bacteriolysis aid for each of the different bacteriolysis enzymes, and prevents a mistake of using a wrong bacteriolysis aid. In addition, even when using two or more bacteriolysis enzymes, it is possible to lyse two or more species of bacteria simultaneously, which makes the bacteriolysis process more efficient and rapid. This also makes it possible to efficiently and rapidly detect bacteria of multiple genera using, e.g., intracellular antigens.

DESCRIPTION OF EMBODIMENTS

Figure 1:
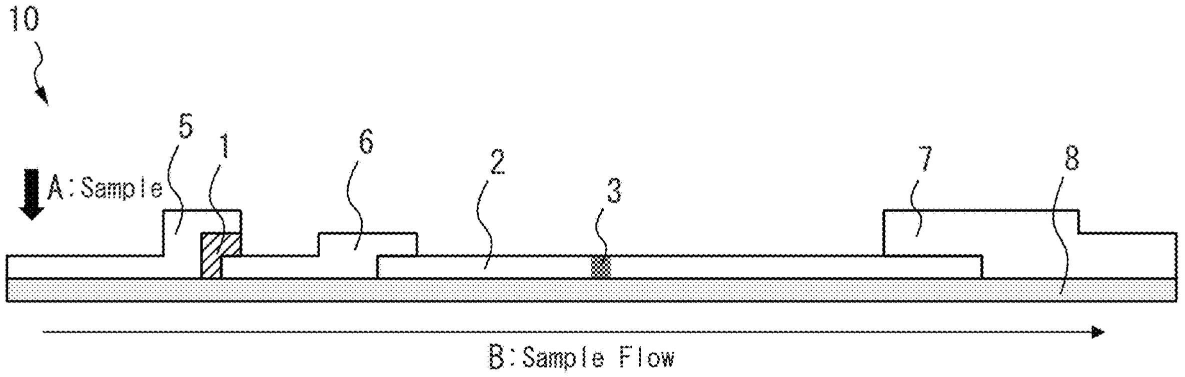
FIG. 1 is a cross-sectional view of a schematic diagram of a strip-shaped detection mechanism as an example of a detection mechanism of a lateral flow type immunochromatographic detection system for detecting at least one bacterial species selected from the group consisting of *Staphylococcus* species, *Escherichia* species, and *Streptococcus* species.

The present invention will be described in detail in accordance with the specific embodiments below. However, the present invention is not bound by the following embodiments, but can be implemented in any form to the extent that it does not depart from the intent of the present invention.

An embodiment of the present invention relates to a method for lysing a group of bacteria in the sample, comprising the step of lysing the group of bacteria in the sample in a mixture solution obtained by mixing the sample, a bacteriolysis enzyme, and a bacteriolysis aid. This step of mixing results in preparation of a mixture solution with a pH and an electrical conductivity each adjusted to a predetermined range, whereby it is possible to lyse and detect bacteria corresponding to the bacteriolysis enzymes used. Other embodiments relate to a bacteriolysis aid for use in the bacteriolysis method, a bacteriolysis kit containing the bacteriolysis aid and bacteriolysis enzymes, and a bacterial detection kit containing the bacteriolysis aid, bacteriolysis enzymes, and a device for detecting a L7/L12 ribosome protein antigen.

I. Bacteriolysis Method

An embodiment of the present invention relates to a bacteriolysis method for lysing a group of bacteria in a sample (hereinafter also referred to as "the bacteriolysis method of the present invention"). The bacteriolysis method of the present invention includes mixing the sample with a bacteriolysis enzyme and a bacteriolysis aid, wherein the bacteriolysis enzyme includes at least one bacteriolysis enzyme selected from the group consisting of lysostaphin, lysozyme, acetyl glucosaminidase, and endopeptidase. The mixture solution is prepared with adjusting the ingredients and concentrations of the bacteriolysis aid such that its pH is from 6.0 to 7.0 and its electrical conductivity is from 2.5 to 8.5 mS/cm (hereinafter also referred to as the predetermined pH range and the predetermined electrical conductivity range, respectively). The upper limit for the predetermined electrical conductivity range may be 8.5, 8.0, 7.5, 7.0, or 6.5, while the lower limit may be 2.6 or 2.7. When the pH and electrical conductivity of the mixture solution are within the predetermined pH range and the predetermined electrical conductivity range, respectively, whereby it is possible to maintain the activity of all of the selected bacteriolysis enzymes and to lyse the bacteria corresponding to the bacteriolysis enzymes. One of the bacteriolysis enzymes may be used, two of the bacteriolysis enzymes may be used, three of the bacteriolysis enzymes may be used, or all four of the bacteriolysis enzymes may be used. The bacteriolysis enzyme may be added to the bacteriolysis aid in advance, or it may be added when mixing the sample and the bacteriolysis aid.

For example, the present invention relates to a bacteriolysis method for lysing a group of bacteria in a sample, including the step of mixing the sample with a bacteriolysis enzyme and a bacteriolysis aid, wherein the bacteriolysis aid has a pH of from 6.0 to 7.0, bacteriolysis aid and an electrical conductivity of from 2.0 to 8.0 mS/cm. In this example, the sample and the bacteriolysis aid are mixed at a predetermined mixing ratio. Bacteriolysis can be carried out with the same bacteriolysis aid and the same predetermined mixing ratio using different bacteriolysis enzymes, whereby it is possible to avoid a mistake of using a wrong bacteriolysis aid. In order to achieve the predetermined pH range and the predetermined electrical conductivity range, the mixing ratio may be within the range of 1:5 to 3:1, preferably 1:3 to 2:1, more preferably 1:2 to 3:2. The mixing ratio is selected such that the resulting mixture solution of the sample and the bacteriolysis aid satisfy the predetermined pH range and the predetermined electrical conductivity range. Mixing the sample and the bacteriolysis aid at this mixing ratio results in a mixture solution having a pH of from 6.0 to 7.0 and an electrical conductivity of from 2.5 to 9.0 mS/cm. Milk to be used as a sample may have different pH and electrical conductivity values due to bacterial infection. However, since the bacteriolysis aid contains a sufficient amount of buffer, there is a high probability that the mixture solution will fall within the predetermined pH range when mixed at the mixing ratio described above, even if the pH of the sample is fluctuating, and considering the fluctuations in the electrical conductivity of the milk, there is also a high probability that the electrical conductivity will fall within the predetermined electrical conductivity range. Therefore, the mixture solution can satisfy the predetermined pH and conductivity ranges if using the aforementioned bacteriolysis aid is used at the aforementioned mixing ratio.

The lysed bacteria group by the bacteriolysis method of the present invention may be subjected to an immunological method, but it may be subjected to other methods for which bacteriolysis is required. The immunological method may be any detection method using an antigen-antibody reaction, such as immunochromatography, western blotting, ELISA, immunoprecipitation, or immunonephelometry, among which immunochromatography using immunochromatography system is especially preferred from the viewpoint of facilitating the testing of samples. The group of two or more species of bacteria to be lysed by the bacteriolysis method of the present invention must be lysed so that they can be detected by immunological methods at a later step. Therefore, the bacteriolysis method of the present invention can also be referred to as a bacteriolysis method for the detection by immunological methods, preferably immunochromatography, and more preferably lateral flow immunochromatography.

The step of lysing the group of bacteria may be any step as long as the sample, the bacteriolysis enzyme, and the bacteriolysis aid are reacted in the mixture solution. For example, the sample, the bacteriolysis enzyme, and the bacteriolysis aid are placed in a container and agitated/mixed so as to cause a reaction. The bacteriolysis enzyme may be added as powder, or it may be placed in the container in advance, or it may be attached to a member of the immunochromatographic device. The bacteriolysis enzyme placed in the container or in a member of the immunochromatographic device is in contact with the sample and the bacteriolysis aid, whereby it is dissolved and reconstituted to exhibit bacteriolysis enzymic activity. The reaction time in the mixture solution containing the sample, the bacteriolysis enzyme, and the bacteriolysis aid is not limited as long as it can cause bacteriolysis. For example, they may preferably be reacted for 10 seconds or more, 30 seconds or more, or one minute or more. The upper limit for the reaction time is not restricted, but from the viewpoint of speeding up the operation, it may preferably be one hour or less, or 30 minutes or less, or 10 minutes or less, or 5 minutes or less. The solution containing the sample, the two or more bacteriolysis enzymes, and the bacteriolysis aid may further be agitated.

In the bacteriolysis method of the present invention, the group of bacteria as the target of bacteriolysis may be selected from the group of bacteria, depending on the bacteriolysis enzyme used, bacteria of the genus *Escherichia* (*Escherichia* species), bacteria of the genus *Staphylococcus* (*Staphylococcus* species), and bacteria of the genus *Streptococcus* (*Streptococcus* species). The group of bacteria as the target of bacteriolysis may include at least one, preferably at least two, more preferably all three, of the three species of bacteria mentioned above. These bacteria are responsible bacteria for mastitis and are important bacteria to detect. The group of bacteria as the target of bacteriolysis may also include other bacteria as long as they can be lysed by the bacteriolysis enzyme according to the present invention. For example, it may include bacteria belonging to the genus *Klebsiella*, the genus *Lactobacillus*, the genus *Pseudomonas*, the genus *Bacillus*, the genus *Serratia*, the genus Rahnella, the genus *Citrobacter*, the genus *Listeria*, the genus *Enterobacter*, and the genus *Salmonella*.

While the bacteriolysis method of the present invention is characterized by mixing the sample, the bacteriolysis enzyme, and the bacteriolysis aid, one or more other ingredients may be further included in the mixture solution as long as the intended bacteriolysis effect is not significantly impaired. These ingredients may be added for the purpose of, e.g., promoting bacteriolysis or allowing detection after bacteriolysis. The bacteriolysis method of the present invention can be carried out as pretreatment in bacterial detection methods. Therefore, the sample lysed by the lysis method of the present invention may be subjected to the immunological assay method either as they are or after further processing.

II. Bacteriolysis Aid

The bacteriolysis aid refers to a solution that is adjusted to achieve, when mixed with the sample and the bacteriolysis enzyme, the predetermined pH and electrical conductivity ranges in the resulting mixture solution. The bacteriolysis aid as used herein has a pH of from 6.0 to 7.0 and an electrical conductivity of from 2.0 to 8.0 mS/cm (hereinafter also referred to as "the bacteriolysis aid of the present invention"). The bacteriolysis aid of the present invention contains a buffer and a surfactant, and may also contain salts.

The bacteriolysis aid of the present invention may further contain optional components that do not interfere with the bacteriolysis reaction or the immunological assay after bacteriolysis. Examples of such optional components include: proteins such as gamma globulin, which may be added to inhibit cross-reactivity in the immunological assay after bacteriolysis; and preservatives, which may be added to enhance the preservation of the bacteriolysis aid. Proteins such as γ globulin can be added to the bacteriolysis aid at a concentration of 1 to 20 μg/ml, more preferably 5 to 15 μg/ml. In addition, a coloring agent may be added to the bacteriolysis aid to indicate that the bacteriolysis aid have been mixed to the sample.

The pH of the bacteriolysis aid may be adjusted with a pH adjuster such as hydrochloric acid and/or sodium hydroxide as appropriate, depending on the type of buffer. Milk samples usually have a pH of about 6.4, but the pH of milk samples from cows with mastitis can vary from 6.0 to 7.8. The type and concentration of the buffer are selected such that even if the pH of the milk sample varies, the pH of the mixture solution after mixing the sample with the bacteriolysis aid stays within the range of from 6.0 to 7.0 (hereinafter referred to as the "predetermined pH").

The electrical conductivity of the bacteriolysis aid varies with the ionic concentration of each component in the bacteriolysis aid. In particular, the type and the concentration of the buffer, which accounts for a significant content, affect the electrical conductivity of the bacteriolysis aid. Furthermore, the concentration of salt can also be used to adjust the electrical conductivity. The electrical conductivity of a solution can be measured with an electrical conductometer. Milk samples usually have an electrical conductivity of about 4 mS/cm, although milk samples from cows with mastitis can vary significantly. The ingredients and their concentrations are selected such that even if the electrical conductivity of the milk sample varies, the electrical conductivity of the mixture solution after mixing the sample with the bacteriolysis aid stays within the range of from 2.5 to 8.5 mS/cm (hereinafter referred to as the "predetermined electrical conductivity"). The upper limit of the predetermined electrical conductivity range may be 8.5, 8.0, 7.5, 7.0, or 6.5, while the lower limit may be 2.6 or 2.7. Among the components of the bacteriolysis aid, the concentrations of salts and buffer considerably affect the electrical conductivity because of their high concentrations. In addition, the mixing ratio of the bacteriolysis aid and the sample is determined to achieve the desired electrical conductivity in the resulting mixture solution.

The buffer to be contained in the bacteriolysis aid may be any buffer as long as it can achieve a pH of 6.0 to 7.0 in the mixture solution after mixing with the sample. Examples of such buffers include, although are not limited to, Tris, MOPSO, HEPES, citric acid, phosphoric acid, and acetic acid, among which Tris and MOPSO are particularly preferred. The concentration of the buffer in the bacteriolysis aid may be appropriately selected to achieve the desired pH and conductivity of the mixture solution after mixing the sample with the bacteriolysis aid. As an example, the final concentration in the mixture solution may be 1.2 to 420 mM, preferably 5 to 100 mM, more preferably 20 to 100 mM. The buffer affects the electrical conductivity of a solution. The concentration of the buffer in the bacteriolysis aid may be determined by considering the mixing ratio of the sample to the bacteriolysis aid and the final concentration in the mixture solution. As an example, the buffer concentration in the bacteriolysis aid may be 5 to 500 mM, preferably 10 to 250 mM, more preferably 20 to 100 mM.

A surfactant may be incorporated in the bacteriolysis aid for the purposes of achieving a chemical bacteriolysis effect or facilitating the measurement by immunological techniques, especially immunochromatographic assays. The surfactant may be any surfactant as long as it does not inhibit the activity of the bacteriolysis enzyme or the measurement by an immunological method after bacteriolysis. For example, sodium dodecyl sulfate is a strong surfactant and can lyse almost all bacteria, but it is not suitable as a surfactant for use in the bacteriolysis method of the present invention because it destroys the structure of antibodies used in immunological techniques. Surfactants that do not interfere with the measurement by immunological techniques, especially immunochromatographic assays after bacteriolysis, include, although are not limited to, anionic surfactants, nonionic surfactants, and zwitterionic surfactants. The concentration of anionic and zwitterionic surfactants affects the electrical conductivity.

Nonionic surfactants may be added primarily for the purpose of ensuring flow of the developing solution when immunochromatography is used after lysis. They may also be used for the purpose of chemical bacteriolysis. Nonionic surfactants are surfactants in which a hydrophilic moiety, such as a polyoxyethylene chain, sorbitan (or its derivative), sugar, ethanolamide, or glycerin, is bonded to a hydrophobic moiety such as an alkyl group or fatty acid. Examples of nonionic surfactants may include, although are not limited to, ester-ether type, ester type, or ether type surfactants, all of which can be suitably used. More specifically, examples of surfactants having polyoxyethylene chains as hydrophilic moieties include polyoxyethylene alkyl ethers, polyoxyethylene alkyl phenyl ethers, Triton™ series, Tergitol™ series, Nonidet™ series, and Genapol™ series. Examples of surfactants having sorbitans (or derivatives thereof) as hydrophilic moieties include fatty acid sorbitan esters and Tween™ series. Examples of nonionic surfactants having other hydrophilic moieties include alkyl polyglucosides, fatty acid diethanol amides, alkyl monoglyceryl ethers.

The balance between hydrophilic and lipophilic properties of nonionic surfactants can be expressed by HLB (hydrophile-lipophile balance) values. From the viewpoint of achieving both bacteriolysis and development in immunochromatography after bacteriolysis, the HLB value may be from 12.0 to 14.5, preferably from 12.1 to 14.4, more preferably from 12.4 to 14.1. HLB values can be determined based on established methods known in the art. As an example, it can be determined by the Griffin, Davis, and Kawakami methods.

Nonionic surfactants having polyoxyethylene chains as hydrophilic moieties can be determined based on the number of repeats of the polyoxyethylene chains. In the present invention, from the viewpoint of achieving both bacteriolysis and post-bacteriolysis development in immunochromatography, they may usually have polyoxyethylene chains with 7 to 11, preferably 7.5 to 10, repeats on average. The polyoxyethylene chain may usually be represented by the following formula:

[Formula 1]

$$H—(CH_2CH_2—O)_n—$$

where n is an integer. Thus, it is expressed by the average number of repetitions depending on the degree of polymerization. Since the molecular weight of ($CH_2$ $CH_2$—O) is 44, the average number of repetitions can be calculated by measuring the average molecular weight of the polyoxyethylene chain. The average molecular weight of the polyoxyethylene chain can be determined by subtracting the molecular weight of the hydrophobic moiety from the average molecular weight of the surfactant molecule. The average molecular weight of the surfactant molecule surfactant can be determined by methods known in the art, such as chromatographic methods including gel permeation chromatography (GPC) and thin layer chromatography (TLC).

According to an embodiment of the present invention, the nonionic surfactant having a polyoxyethylene chain as a hydrophilic moiety may have an HLB value of 12.0 or more but less than 14.5, preferably from 12.1 to 14.4, still more preferably from 12.4 to 14.1, and an average number of repetitions of from 7 to 11, preferably from 7.5 to 10. Such a nonionic surfactant is referred to as a first nonionic surfactant. Use of the first nonionic surfactant allows bacteriolysis of targets including *Escherichia* species, *Staphylococcus* species, and *Streptococcus* species and/or detection of these bacteria using immunochromatography. Examples of such nonionic surfactants include Triton™ X100, Nonidet™ P40, Triton™ X-100 (reduced), Genapol™ X-080, TERGITOL™ 15-S-9, TERGITOL™ TMN-100X (90%), TERGITOL™ TMN-6 (90%), Triton™ X114, TERGITOL™ 15-S-7, and TERGITOL™ TMN-10 (90%).

The concentration of nonionic surfactant is not restricted, as long as it does not significantly interfere with the bacteriolysis by the bacteriolysis method of the present invention, the development in immunochromatographic detection after bacteriolysis, and the antigen-antibody reaction in immunoassay methods. According to an example, the concentration of the nonionic surfactant in the mixture solution of the sample and the bacteriolysis aid may be 0.65% to 5%. According to an example, the concentration of the nonionic surfactant may be 1% or more, more preferably 1.25% or more. On the other hand, from the viewpoint of not significantly inhibiting the reaction by the bacteriolysis enzyme or the antigen-antibody reaction, the concentration of nonionic surfactant may be 4% or less, more preferably 3.125% or less. The concentration of the nonionic surfactant in the bacteriolysis aid can be determined by considering the mixing ratio of the sample to the bacteriolysis aid and the ratio of the bacteriolysis aid after mixing. As an example, the nonionic surfactant may be mixed in the lysis aid at a concentration of from 0.55% to 20%, preferably from 1% to 10%, more preferably from 2% to 5%.

Anionic surfactants are added primarily for chemical bacteriolysis. Examples of anionic surfactants include: sodium alkyl sulfates; sodium N-acylsarcosinates such as sodium N-dodecanoylsarcosinate, sodium N-lauroylsarcosinate, sodium N-myristoylsarcosinate; N-acylglutamates such as sodium dodecylbenzenesulfonate, sodium hydrogenated coconut fatty acid monoglyceride monosulfate, sodium lauryl sulfoacetate, and sodium N-palmitoylglutamate; sodium N-methyl-N-acylalanine; and sodium alpha-olefin sulfonates. The content of the anionic surfactant (when two or more anionic surfactants are used, the total content of the anionic surfactants) in the bacteriolysis aid is not limited as long as the effective bacteriolysis rate for detection is ensured. Specifically, regardless of the content of the bacteriolysis enzyme, the content of the anionic surfactant in the bacteriolysis aid can be determined such that the final concentration in the mixture solution when mixed with milk is 0.01% or more, preferably 0.05% or more, more preferably 0.1% or more. The upper limit of the anionic surfactant content is not limited as long as it does not significantly inhibit the reaction by the bacteriolysis enzyme or the antigen-antibody reaction. Specifically, in any case, it may be 2% or less, preferably 1% or less, more preferably 0.5% or less. The concentration of the anionic surfactant in the bacteriolysis aid can be determined by considering the mixing ratio of the sample to the bacteriolysis aid and the final concentration of the bacteriolysis aid. As an example, the anionic surfactant may be added to the bacteriolysis aid at a concentration of from 0.012% to 8%, preferably from 0.05% to 4%, more preferably from 0.1% to 1%.

Zwitterionic surfactants are added primarily for chemical bacteriolysis. Examples of zwitterionic surfactants include: amino acid-based surfactants (alkylamino fatty acid salts), betaine-based surfactants (alkyl betaines), and amine oxide-based surfactants (alkylamine oxides). More specific examples include dimethylammoniopropanesulfonate, dodecyldimethylammonio-butyrate, betaine laurylate, and amidopropyl betaine. More specific examples include Zwittergent™ series zwitterionic surfactants. Surfactants of Zwittergent™ series that can be used include Zwittergent™ 3-14, Zwittergent™ 3-12, Zwittergent™ 3-10, and Zwittergent™ 3-8. The content of the zwitterionic surfactant in the bacteriolysis aid is not limited as long as the effective bacteriolysis rate for detection is ensured. Specifically, regardless of the content of the bacteriolysis enzyme, the content of the zwitterionic surfactant in the bacteriolysis aid can be determined such that the final concentration in the mixture solution when mixed with milk is 0.01% or more, preferably 0.05% or more, more preferably 0.1% or more. The upper limit of the zwitterionic surfactant content is not limited as long as it does not significantly inhibit the reaction by the bacteriolysis enzyme or the antigen-antibody reaction. Specifically, in any case, it may be 2% or less, preferably 1% or less, more preferably 0.5% or less. The concentration of the zwitterionic surfactant in the bacteriolysis aid can be determined by considering the mixing ratio of the sample to the bacteriolysis aid and the final concentration of the bacteriolysis aid. As an example, the zwitterionic surfactant may be added to the bacteriolysis aid at a concentration of from 0.012% to 8%, preferably from 0.05% to 4%, more preferably from 0.1% to 1%.

Salts may be contained in the bacteriolysis aid to adjust the electrical conductivity. Salts may be any salts as long as they do not interfere with the bacteriolysis and the post-bacteriolysis measurement by immunological methods. Examples include sodium chloride, sodium sulfate, and potassium chloride. From the viewpoint of adjusting the electrical conductivity of the bacteriolysis aid to within the range of from 2 to 8 mS/cm, the concentration of the salts may be determined as appropriate. For example, the salts may be added to the bacteriolysis aid at a concentration of from 15 mM to 75 mM, preferably from 20 to 60 mM, more preferably from 30 to 50 mM.

III. Bacteriolysis Enzyme

The bacteriolysis enzyme refers to an enzyme that lyses bacteria in a sample. Such bacteriolysis enzymes are selected from the group consisting of lysostaphin, lysozyme, acetylglucosaminidase, and endopeptidase. At least one, at least two, at least three, or all four, of these bacteriolysis enzymes may be used. These enzymes may be provided as a complex enzyme. For example, acetyl glucosaminidase is prepared from the culture supernatant of *Streptomyces fulvissimus*, especially strain TU-6, and is sold under the name Labiase. In addition to acetylglucosaminidase activity, labiase is known to have endopeptidase and muramidase (lysozyme) activity, and known to be a complex enzyme. Therefore, labiase may be excluded from the scope of the present invention. For example, when at least two bacteriolysis enzymes are used, the combination of lysozyme and acetyl glucosaminidase, the combination of lysozyme and endopeptidase, and the combination of endopeptidase and acetyl glucosaminidase may be excluded, depending on the conditions. When at least three bacteriolysis enzymes are used, the combination of lysozyme, acetyl glucosaminidase, and endopeptidase may be excluded, depending on the conditions. The bacteriolysis enzyme may be provided in powder form, as a concentrated solution, or as a member to which the bacteriolysis enzyme is attached, dried, and solidified. The bacteriolysis enzyme may be added to the bacteriolysis aid in advance, or may be mixed with the sample and the bacteriolysis aid upon use. For example, the bacteriolysis enzyme may be dry adhered to the liquid immersion site of the immunochromatographic device such that when the immunochromatographic device is used, the bacteriolysis enzyme is eluted and mixed with the sample and the bacteriolysis aid. In another example, the bacteriolysis enzyme may be adhered as a dry powder in the container in which the sample and the bacteriolysis aid are mixed.

The concentration of the bacteriolysis enzyme in the bacteriolysis method of the present invention is not restricted, but may be determined depending on the type of the bacteriolysis enzyme. From the viewpoint of achieving its bacteriolysis effect, the concentration of the bacteriolysis enzyme in the solution at the time of reaction with the sample may be 0.01 μg/mL or more, or 0.025 μg/mL or more, or 0.05 μg/mL or more. On the other hand, from the viewpoint of not generating false positives in the immunological method of testing, the concentration of the bacteriolysis enzyme may be 20 mg/mL or less, 100 mg/mL or less, or 50 mg/mL or less.

Lysozyme is a single peptide protein of approximately 14.6 kDa that cleaves the β(1-4) glycosidic bond between N-acetylmuramic acid and N-acetylglucosamine at the peptidoglycan layer, whereby bacterial cells can be lysed. Lysozyme can lyse bacteria of, although are not limited to, the genus *Escherichia* (*Escherichia* species) and the genus *Klebsiella* (*Klebsiella* species). Lysozyme can be obtained through commercial purchase. The final concentration of lysozyme when mixed with the sample may be 0.1 mg/mL or more, preferably 0.5 mg/mL or more, and more preferably 1.0 mg/mL or more. The upper limit of the content of the bacteriolysis enzyme can be determined from an economic viewpoint, and in any case, the lower limit may be 200 mg/mL or less, preferably 100 mg/mL or less, and more preferably 50 mg/mL or less.

Labiase is a complex enzyme consisting mainly of β-N-acetyl-D-glucosaminidase, muramidase, and endopeptidase, prepared from the supernatant of culture medium of *Streptomyces fulvissimus* TU-6 strain. Labiases can lyse bacteria of, although are not limited to, the genus *Streptococcus*, the genus *Bacillus*. and the genus *Lactobacillus*. Labiase can be prepared from the culture supernatant of the above strains or can be obtained through commercial purchase. The final concentration of labiase when mixed with the sample may be preferably 0.05 mg/mL or more, preferably 0.1 mg/mL or more, more preferably 0.3 mg/mL or more. The upper limit of the content of the bacteriolysis enzyme can be determined from an economic viewpoint, and in any case, the lower limit may be 20 mg/mL or less, preferably 10 mg/mL or less, more preferably 5 mg/mL or less.

Lysostaphin is a zinc protease produced by *Staphylococcuss imulans* and hydrolyzes glycylglycine bonds in the glycopeptide chains of the cell wall peptidoglycan of *Staphylococcus aureus* or its allies. Accordingly, lysostaphin can lyse bacteria of, although are not limited to, the genus *Staphylococcus* (*Staphylococcus* species). Lysostaphins as used herein include naturally-occurring lysostaphin and mutated and/or modified lysostaphin, in which mutations or modifications are introduced to the extent that hydrolytic activity is not lost. These lysostaphin may be obtained via the culture method or the genetic engineering described in JP-H11-28099 A or obtained through commercial purchase. The final concentration of lysostaphin when mixed with the sample may be 0.1 μg/mL or more, preferably 0.5 μg/mL or more, more preferably 1.0 μg/mL or more. The upper limit of the content of the bacteriolysis enzyme can be determined from an economic viewpoint, and in any case, the lower limit may be 200 μg/mL or less, preferably 100 μg/mL or less, more preferably 50 μg/mL or less.

IV. Sample

The sample to be used in the present invention may be any sample that needs to be tested for the presence or absence of bacteria. An example of the sample is milk. The milk may be of any animal origin, but especially milk of bovine origin. The pH of milk is usually about 6.4, and the electrical conductivity of milk is usually about 4 mS/cm. On the other hand, if the udder has bacterial infection and is inflamed, the pH and electrical conductivity of the milk can fluctuate. The pH of milk from individuals with bacterial infection and mastitis can vary from 6.0 to 7.8.

V. Bacterial Detection Method

The bacteriolysis method according to the present invention can be performed as a pre-step of the bacterial detection method. After the method of lysing the group of bacteria in the sample, a method of detecting bacteria or a method of determining the presence or absence of bacteria (hereinafter also referred to as "the bacterial detection method of the present invention") may be carried out. The bacterial detection method of the present invention includes the steps of: lysing the group of bacteria in the sample by carrying out the bacteriolysis method of the present invention; and detecting bacterial antigens released from a lysed bacteria using antibodies that can cause antigen-antibody reactions with the antigens. More specifically, the method allows for the determination of the presence or absence of at least one species of bacteria selected from the group consisting of *Escherichia* species, *Staphylococcus* species, and *Streptococcus* species in a sample. The method includes the steps of:

mixing the sample, a bacteriolysis enzyme, and a bacteriolysis aid to prepare a mixture solution; and detecting L7/L12 ribosome proteins by an immunological method, wherein the bacteriolysis enzyme includes at least one bacteriolysis enzyme selected from the group consisting of lysostaphin, lysozyme, acetyl glucosaminidase, and endopeptidase.

In this method, the mixture solution has a pH of from 6.0 to 7.0, the mixture solution has an electrical conductivity of from 2.5 to 8.5 mS/cm. The method of the present invention may be characterized in that the lysozyme can lyse the *Escherichia* species, the lysostaphin can lyse the *Staphylococcus* species, and the lysozyme, acetyl glucosaminidase, and endopeptidase can lyse the *Streptococcus* species. Therefore, the bacterial detection method of the present invention relates to immunological methods using antibodies. Immunological methods may be any detection methods using antigen antibody reactions, such as immunochromatography, immunoprecipitation, immunoturbidimetry, enzyme immunoassay (ELISA), radioimmunoassay (RIA), or fluorescence immunoassay (FIA). From the viewpoint of simplifying the testing of samples, immunochromatography is especially preferred, and lateral flow type immunochromatography is even more preferred.

According to the bacterial detection method of the present invention, the bacterial antigens may preferably be intracellular antigens. The intracellular antigen refers to a bacterial intracellular substance released by the bacteriolysis method of the present invention. More specifically, from the viewpoint of detecting bacteria, the intracellular antigen may preferably be a ribosomal protein, especially the L7/L12 ribosomal protein. L7/L12 ribosomal protein is a type of ribosomal protein that is essential for microbial protein synthesis and is commonly possessed by various bacteria. In addition, L7/L12 ribosomal protein has high detection sensitivity due to the presence of multiple molecules in the cell. For antibodies that cause antigen-antibody reactions against bacterial L7/L12 ribosomal proteins and production methods thereof, see, e.g., WO2000/006603 A, the international patent publication of an earlier patent application filed by the present applicant. Immunochromatography uses a labelling antibody with a detection label and a capture antibody immobilized on a strip. The labelling antibody and the capture antibody each bind to an intracellular antigen.

VI. Antibodies

The term "antibody" used herein refers to a protein that recognizes and binds to a specific antigen or substance, which may also be referred to as an immunoglobulin (Ig). Common antibodies typically have two light chains (light chains) and two heavy chains (heavy chains) that are interconnected by disulfide bonds. There are two classes of light chains, called λ and κ chains, and five classes of heavy chains, called γ, μ, α, δ, and ε chains. Depending on the class of their heavy chains, antibodies are classified into five isotypes: IgG, IgM, IgA, IgD and IgE, respectively.

Heavy chains each include a heavy chain constant (CH) region and a heavy chain variable (VH) region. Light chains each include a light chain constant (CL) region and a light chain variable (VL) region. The light chain constant (CL) region consists of a single domain. The heavy chain constant (CH) region consists of three domains, namely CH1, CH2, and CH3. The light chain variable (VL) region and the heavy chain variable (VH) region each consist of four highly conserved regions called framework regions (FRs; FR-1, FR-2, FR-3, and FR-4) and three hypervariable regions called complementarity-determining regions (CDRs; CDR-1, CDR-2, and CDR-3). The heavy chain constant (CH) region consists of three CDRs (CDR-H1, CDR-H2, and CDR-H3) and four FRs (FR-H1, FR-H2, FR-H3, and FR-H4), which are arranged from the amino terminus to the carboxy terminus in the order of FR-H1, CDR-H1, FR-H2, CDR-H2, FR-H3, CDR-H3, and FR-H4. The light chain constant (CL) region has three CDRs (CDR-L1, CDR-L2, CDR-L3) and four FRs (FR-L1, FR-L2, FR L3, and FR-L4), which are arranged from the amino terminus to the carboxy terminus in the order of FR-L1, CDR-L1, FR-L2, CDR-L2, FR-L3, CDR-L3, and FR-L4. The variable regions of the heavy and light chains contain binding domains that interact with the antigen.

The antibody of the present invention may be either a polyclonal antibody or a monoclonal antibody, but a monoclonal antibody be preferred. A polyclonal antibody is usually prepared from the serum of an animal immunized with an antigen and is a mixture of various antibody molecules with different structures. A monoclonal antibody, on the other hand, is an antibody composed of a single type of molecules containing a combination of light chain variable (VL) and heavy chain variable (VH) regions having determined amino acid sequences. Monoclonal antibodies can be produced from clones derived from antibody-producing cells, or they can be produced using genetic engineering technique, by obtaining nucleic acid molecules having gene sequences encoding amino acids of antibody proteins. It is also a well-known technique to those skilled in the art to improve the binding and specificity of antibodies using genetic information of their heavy chains and light chains or their variable regions and CDRs.

The antibody of the present invention may be a fragment and/or derivative of an antibody. Fragments of antibodies include $F(ab')_2$, Fab, Fv, etc. Antibody derivatives include antibodies in which amino acid mutations have been artificially introduced into the constant region(s) of the light and/or heavy chains, antibodies in which the domain configuration of the constant region(s) of the light and/or heavy chains has been modified, antibodies with two or more Fc regions per molecule, glycosylated antibodies, bispecific antibodies, antibody conjugates in which an antibody or antibody fragment is bound to a protein other than the antibody, antibody enzymes, antibody conjugates in which an antibody or antibody fragment is bound to a protein other than an antibody, etc. Antibody conjugates, antibody enzymes, tandem scFv, bispecific tandem scFv, diabody, etc. Furthermore, when the aforementioned antibodies or their fragments or derivatives are derived from non-human animals, chimeric or humanized antibodies in which some or all of the sequences other than the CDRs thereof are replaced with the corresponding sequences of human antibodies are also included in the scope of the antibody of the present invention. When the simple term “antibodies” is used herein, it is intended to also encompass fragments and/or derivatives of antibodies, unless otherwise specified.

When the antibody of the present invention causes antigen-antibody reactions with certain bacteria, it means that they bind specifically to some components of the bacteria as antigens. The components of bacteria that serve as antigens for the antibody of the present invention are not limited. It may be a component contained in the cell walls or cell membranes that are exposed outside the bacterial cells, or it may be a component contained in the cytoplasm, cell organelles, or nucleus and not exposed outside the bacterial cells.

The degree of antigen-antibody reaction between the antibody of the present invention and the bacteria to be detected is not particularly limited, but the antigen-antibody reaction may occur at least to the extent that it can be detected by some known detection method.

The antibody of the present invention may also preferably not cause any cross-reactions with one or more non-bacterial components that may be present in the sample. Examples of such non-bacterial components include, although are not limited to, various bioorganic compounds derived from viruses, plants, and/or animals that are not present in bacteria. Specific examples of such bioorganic compounds include proteins, sugars, glycoproteins, lipids, complex lipids, and nucleic acids. The antibody of the present invention may preferably not cause any cross-reactions with components derived from at least one, or 2 or more, or 3 or more, or 4 or more, or 5 or more, or 6 or more, or 7 or more, or 8 or more, especially 9 or more, most preferably 10 or more, of these non-bacterial components.

The antibody of the present invention is not limited as long as it can cause an antigen-antibody reaction with the bacteria to be detected, but the generic antibody and/or the specific antibody explained below may be preferably used. Especially when bacterial antigens are detected via a sandwich-type mode, the generic antibody and the specific antibody may preferably be used in combination. The generic antibody may preferably cause an antigen-antibody reaction widely with as many genera of bacteria as possible. Specifically, the generic antibody may cause an antigen-antibody reaction with at least four genera of bacteria, preferably with at least five or more genera of bacteria, more preferably with at least six or more genera of bacteria. The genera of specific bacteria with which the generic antibody causes an antigen-antibody reaction are not limited, but the generic antibody may preferably cause an antigen-antibody reaction with at least bacteria belonging to one or more species of genera selected from the genus *Escherichia*, the genus *Staphylococcus*, the genus *Streptococcus*, the genus *Pseudomonas*, the genus *Bacillus*, the genus *Klebsiella*, the genus *Serratia*, the genus Rahnella, the genus *Citrobacter*, the genus *Listeria*, the genus *Enterobacter*, and the genus *Salmonella*. More preferably, the generic antibody may preferably cause an antigen-antibody reaction with at least bacteria belonging to the genus *Escherichia*, the genus *Staphylococcus*, and the genus *Streptococcus*, which are pathogenic bacteria for mastitis.

On the other hand, the specific antibody may preferably cause antigen-antibody reactions only with bacteria of limited genera. Specifically, the range of bacteria with which the specific antibody causes antigen-antibody reactions may preferably be commensurate with the range of bacteria to be detected. When only a single specific antibody is used, the range of bacteria for which the specific antibody causes antigen-antibody reactions may be commensurate with the range of bacteria to be detected. On the other hand, when two or more specific antibodies are used in combination, the combined range of bacteria with which the specific antibodies cause antigen-antibody reactions in combination may be commensurate with the range of bacteria to be detected. The latter embodiment is particularly advantageous because it makes it possible to adjust the range of bacteria to be detected in various ways by appropriately combining plural specific antibodies that each cause antigen-antibody reactions with different bacteria.

Each specific antibody of the present invention may cause antigen-antibody reactions with at least one genus of bacteria. The specific bacterial genera with which each specific antibody causes antigen-antibody reactions are not limited, but each specific antibody may preferably cause antigen-antibody reactions at least with bacteria of one or more genera selected from the genus *Escherichia*, the genus *Staphylococcus, Pseudomonas* genus (*Pseudomonas*), the genus *Bacillus*, the genus *Klebsiella*, the genus *Serratia*, the genus Rahnella, the genus *Citrobacter*, the genus *Listeria*, the genus *Enterobacter*, and the genus *Salmonella*. More preferably, each specific antibody may preferably cause an antigen-antibody reaction with at least bacteria belonging to the genus *Escherichia*, the genus *Staphylococcus*, and the genus *Streptococcus*, which are pathogenic bacteria for mastitis.

[Labeling Antibody]

The labeling antibody is an antibody that is labeled for detection and forms a complex with the antigen derived from the target bacteria released from the lysed target bacteria via an antigen-antibody reaction. The complex thus formed may also be referred to as a first complex. The type of detection label used for the labeling antibody is not restricted and may be selected as appropriate in accordance with the detection method. Specific examples include: metal colloids such as gold colloids, platinum colloids, and palladium colloids; non-metal colloids such as selenium colloids, alumina colloids, and silica colloids; insoluble granular materials such as colored resin particles, dye colloids, colored liposomes, etc.; enzymes that catalyze chromogenic reactions such as alkaline phosphatase, peroxidase, luciferase, etc.; fluorescent dyes, radioisotopes; and chemiluminescent labels, bioluminescent labels, electrochemiluminescent labels, etc. The method for attaching the label to the antibody is also not restricted, but specific examples of methods that can be used include physical adsorption using the hydrophobicity of the antibody, chemisorption using a functional group of the antibody, etc.

[Capture Antibody]

The capture antibody is an antibody that forms a complex with the first complex based on an antigen-antibody reaction. The complex thus formed may also be referred to as a second complex. When used in immunochromatography, the capture antibody may more specifically be immobilized on a membrane support for chromatographic development located in the detection region of the immunochromatographic strip. There are no restrictions on the method used to immobilize the antibody on the solid-phase material. Examples of specific methods include immobilization by physisorption using the hydrophobicity of the antibody and immobilization by chemical bonding using the functional groups of the antibody.

The generic antibody may be the labeling antibody, and the specific antibody may be the capture antibody. Alternatively, the specific antibody may be the labeling antibody, and the generic antibody may be the capture antibody. However, from the viewpoint of facilitating the production of the immunochromatographic detection device, it may be preferable that the generic antibody is the labeling antibody and the specific antibody is the capture antibody.

The second complex is held at the position where the capture antibody is immobilized (capture site) via an antigen-antibody reaction with the immobilized capture antibody, and where the labeling of the labeling antibody is detected. If the label is detected at the position where the capture antibody is immobilized, then the target bacteria are detected in the sample solution.

VII. Kit

Another embodiment of the present invention relates to a bacteriolysis kit to be used in the bacteriolysis method of the present invention, for lysing a group of bacteria in a sample (hereinafter also referred to as "the bacteriolysis kit of the present invention"). The bacteriolysis kit of the present invention contains at least one bacteriolysis enzyme selected from the group consisting of lysostaphin, lysozyme, and labiase, and the bacteriolysis aid of the present invention. The bacteriolysis kit may be provided as a pre-mixed bacteriolysis solution as a mixture of the bacteriolysis enzyme and the bacteriolysis aid. The bacteriolysis kit is used for detecting a group of bacteria by immunoassay after bacteriolysis, and more preferably, it is related to bacteriolysis kits for immunochromatographic detection. The details of the target bacteria to be lysed, the surfactant in the bacteriolysis aid, and the bacteriolysis enzyme are as described above. The bacteriolysis kit may be provide with the bacteriolysis enzyme in the form of a solution or powder or as attached to a member such as fiberglass.

Still another embodiment of the present invention relates to a bacteria detection kit to be used in the bacterial detection method of the present invention, for detecting a group of bacteria in a sample (hereinafter also referred to as "the bacterial detection kit of the present invention"). The bacterial detection kit of the present invention may contain the bacteriolysis kit of the present invention and a device for detecting a L7/L12 ribosome protein antigen, or may contain at least one bacteriolysis enzyme selected from the group consisting of lysostaphin, lysozyme, acetyl glucosaminidase, and endopeptidase, the bacteriolysis aid of the present invention, and a device for detecting a L7/L12 ribosome protein antigen. It may further contain a container for mixing the sample, the bacteriolysis aid, and the bacteriolysis enzyme, as well as instructions for the product. The details of the bacteriolysis enzyme and the bacteriolysis aid to be used in the bacterial detection kit of the present invention are as described above. The device for detecting a L7/L12 ribosome protein antigen according to the present invention may be any device as long as it allows for the detection of an L7/L12 ribosome protein antigen by an immunological method, and may be an immunochromatographic device. The immunochromatographic device may contain the capture antibody and the labeling antibody explained above. The capture antibody is provided in an appropriate form depending on the type of the solid phase carrier (e.g., a container having a porous membrane, a container having a flow channel, a plate for retaining solution, etc.). In one example, the captured antibody is immobilized on a membrane carrier for chromatographic development located in the detection region of the strip of the immunochromatographic device. The labeling antibody is usually provided in the form of an aqueous reagent containing the labeling antibody in an aqueous medium or a dried reagent in which the labeling antibody is dried. It is also possible to use a single immunochromatographic system with two or more labeling antibodies and two or more capture antibodies for different bacteria. The two or more capture antibodies are fixed separately on the membrane carrier for chromatographic development located in the detection area of the strip. This allows detection of L7/L12 ribosomal protein antigens from different bacteria, each labeled by a labeling antibody and captured by a capture antibody at a predetermined position.

The bacterium detection kit of the present invention includes, in addition to the capture antibody and the detection antibody explained above, one or more reagents and a detection device or components thereof necessary to perform the method of the present invention using these antibodies, and/or instructions describing the procedure for performing the method of the present invention. The type of such reagents and instructions, as well as other components included in the kit of the present invention, may be determined according to the specific immunological assay used to detect bacteria of plural genera.

When the bacterium detection kit of the present invention contains a device for detection or components thereof, the device assembled from the kit is a device equipped with components necessary for performing the method of the present invention using the labeling antibody and/or the capture antibody of the present invention (hereinafter also referred to as "the device of the present invention"). The specific components of the device of the present invention may be determined according to the type of immunological assay as a specific embodiment of the method of the present invention. As explained above, examples of immunological assay methods using two or more antibodies include, although are not limited to, various known immunological assays such as ELISA using antibody-loaded microtiter plates; latex particle agglutination assay using latex particles (e.g. polystyrene latex particles) loaded with antibodies; immunochromatography using antibody-loaded membranes; and sandwich assay using a detection antibody labeled with colored or chromogenic particles, enzymes or fluorophores, etc., and a capture antibody immobilized on a solid phase carrier such as magnetic particles. Devices equipped with components necessary to perform such various immunological assays may be used as the device of the present invention. Two or more species of bacteria in a sample can also be detected with a single capture antibody-immobilized site. In this case, one or more species are immobilized on a single capture antibody-immobilized site. This single capture antibody-immobilized (linkage) site may be used for detecting two or more species of bacteria in a sample simultaneously (detection of the total amount of bacteria).

Specific examples of immunochromatographic detection devices include devices of the lateral-flow type and those of the flow-through type. According to the lateral-flow devices, the analyte to be detected and the antibody to be detected are deployed parallel onto a membrane having a detection area on the surface of which the capture antibody is immobilized, and the target substance captured in the detection area of the membrane is detected. Lateral flow kits can be generally classified into two main types: dipstick type and cassette type. According to the dipstick type, the sample solution is spread by immersing an immersion area (or a sample pad) of the detection device in the sample solution, whereas according to the cassette type, the sample solution is spread by adding the sample to the sample addition member (sample pad) (3) of the detection device. On the other hand, according to the flow-through devices, the analyte to be detected and the detection antibody are passed vertically through a membrane on which the capture antibody is immobilized on the surface, and the target substance captured on the membrane surface is detected. The method of the present invention can be applied to both lateral-flow devices and flow-through devices.

Both lateral-flow type and flow-through type immunochromatographic detection devices are well known, and the details of such devices can be designed by those skilled in the art based on their technical knowledge, other than those described herein. The following is a description of the schematic configuration of the detection mechanism of the lateral flow type immunochromatographic detection device, with reference to the drawings. However, these are only examples of the schematic configuration of the detection procedure, and the configuration of the lateral-flow type immunochromatographic detection system is not limited in any way to the embodiment illustrated in the figure.

Figure 2:
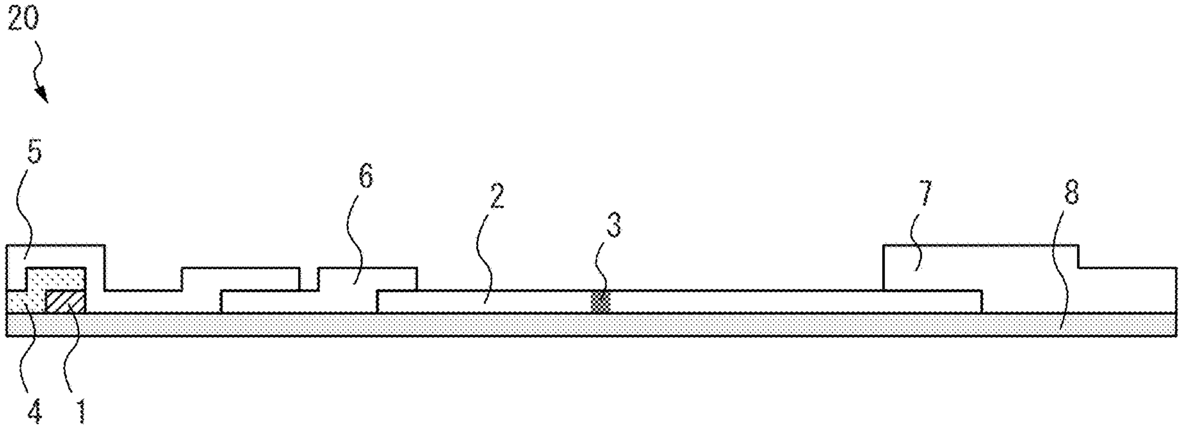
FIG. 2 is a cross-sectional view of a schematic diagram of a strip-shaped detection mechanism as an example of a detection mechanism of a lateral flow type immunochromatographic detection system for detecting *Staphylococcus* species.
Figure 3:
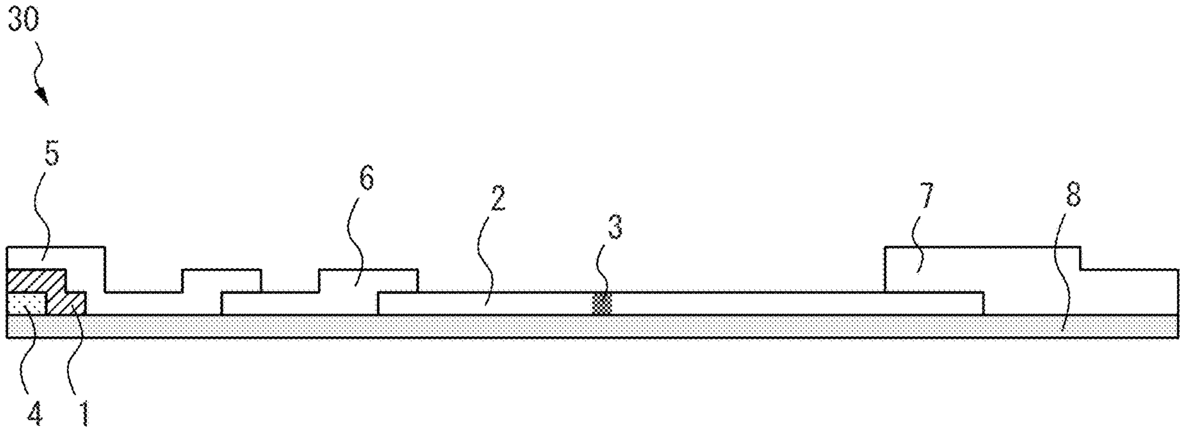
FIG. 3 is a cross-sectional view of a schematic diagram of a strip-shaped detection mechanism as an example of a detection mechanism of a lateral flow type immunochromatographic detection system for detecting *Escherichia* species.
Figure 4:
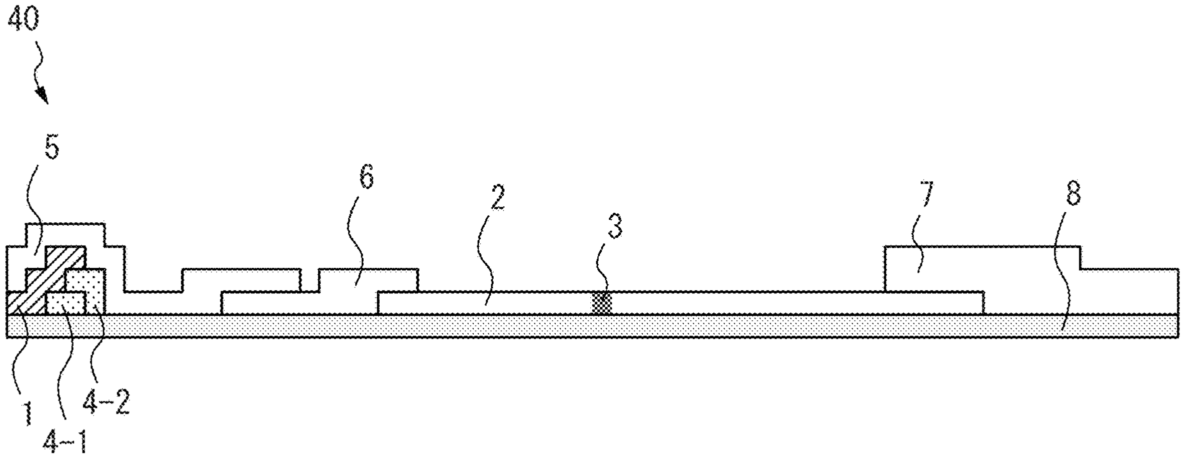
FIG. 4 is a cross-sectional view of a schematic diagram of a strip-shaped detection mechanism as an example of a detection mechanism of a lateral flow type immunochromatographic detection system for detecting *Streptococcus* species.

FIGS. 1 to 4 are cross-sectional views each indicating a schematic configuration of a strip-shaped detection mechanism, which is an example of a detection mechanism of a lateral-flow type immunochromatographic detection system. The immunochromatographic detection device 10 shown in each of FIGS. 1 to 4 contains a membrane carrier for chromatographic development 2, a filter member 6 and a sample contact member (sample pad) 5 arranged at one end thereof (on the upstream side of sample flow B), and an absorption member (absorption pad) 7 arranged on the other end thereof (on the downstream side of sample flow B), on a base material 8. The sample contact member 5 is a member that is to be in contact with the sample and may be any member as long as it does not interfere with the deployment of the sample. The sample contact member 5 and the filter member 6 have a retention particle size that can remove solids and fat globules contained in the sample. The retention particle size of the sample contact member 5 can be set larger than that of the filter member 6 such that relatively large particles are removed by the sample contact member 5, followed by smaller particles by the filter member 6. The removal of solids and particles larger than a certain particle size avoids poor development in the membrane carrier for chromatographic development. The labeling antibody-attached member (conjugate pad) 1 (to which the labeling antibody is attached) is placed upstream of the membrane carrier for chromatographic development 2 such that the attached antibody is developed on the membrane carrier for chromatographic development. The labeling antibody-attached member (conjugate pad) 1 may be placed at the connection position between the sample contact member (sample pad) 5 and the filter member 6 (FIG. 1) or inside the upstream end of the sample contact member (sample pad) 5 (FIGS. 2 to 4). The labeling antibody-attached member (conjugate pad) 1 may be placed at the upstream end of the sample contact member (sample pad) 5 such that the labeling antibody attached to the labeling antibody-attached member (conjugate pad) 1 elutes into the sample solution. Like the labeling antibody-attached member (conjugate pad) 1, the bacteriolysis enzyme-attached member 4 may be arranged placed at the upstream end of the sample contact member (sample pad) 5 such that the bacteriolysis enzyme elutes into the solution (FIGS. 2 to 4). A middle region of the strip lengthwise direction of the membrane carrier for chromatographic development 2 include a capture site 3, on which the capture antibody is immobilized, as well as a site on which a control reagent is fixed if necessary. The control reagent is a reagent that does not bind to the analyte but does bind to the labeling antibody. The bacteriolysis agent may also be placed on this strip to allow elution of the bacteriolysis agent into the sample solution. Labeling antibodies for detection of *Escherichia* species, *Staphylococcus* species, and *Streptococcus* species may be attached to the labeling antibody-attached member, respectively. In this case, capture antibodies for capturing *Escherichia* species, *Staphylococcus* species, and *Streptococcus* species may be placed separately on the chromatographic substrate, whereby each bacterial species can be detected based on the labeling generated at the capture site.

At the time of use, when a sample A is applied on the sample contact member (sample pad) 5, the sample A passes through the labeling antibody-attached member (conjugate pad) 1, which is impregnated with the labeling antibody, and also through the filter member, and flows through the membrane carrier for chromatographic development 2 in the sample flow direction B. During this process, the analyte in the sample (in the case of the present invention, bacteria to be detected) binds to the labeling antibody to form an analyte-labeling antibody complex (first complex). When the sample A passes through the capture antibody-immobilized site 3, the analyte in the sample binds to the capture antibody to form a capture antibody-analyte-labeling antibody complex (second complex). When the sample A passes through the control reagent-immobilized site, the labeling antibody that has not bound to the analyte binds to the control reagent, whereby it is confirmed that the test has been completed (i.e., that sample A has passed through the capture site 3). The presence or amount of the analyte can be detected by detecting the label of the labeling antibody in the capture antibody-analyte-labeling antibody complex (second complex) that exists in the capture site 2 by known means. If necessary, the label of the labeling antibody may be sensitized by known methods to facilitate detection.

The labeling antibody-attached member (conjugate pad) 1, the bacteriolysis enzyme-attached member 4, the filter member 6, the sample contact member (sample pad) 5, and/or the control reagent-immobilized site may be optionally omitted. When the present mechanism lacks the labeling antibody-attached member (conjugate pad) 1 and/or the bacteriolysis enzyme-attached member 4, he same test as above can be performed by applying the sample A and the labeling antibody and/or the bacteriolysis enzyme, in a pre-mixed state or separately, simultaneously or sequentially, to one end on the membrane carrier for chromatographic development 2.

Even when the capture antibody and the labeling antibody are interchanged, a detection kit can be constructed to enable the same detection.

An embodiment of the present invention may relate to a bacterial detection kit containing the bacteriolysis aid according to the present invention and the lateral flow type immunochromatographic detection device according to the present invention. The bacterial detection kit may also contain additional bacteriolysis enzymes for addition according to the bacteria to be detected. Instead of providing bacteriolysis enzymes for addition, such additional bacteriolysis enzymes may be attached to the bacteriolysis enzyme-attached member 4 of the lateral flow type immunochromatographic detection device. The detection device may be at least one selected from a device for detecting *Escherichia* species, a device for detecting *Staphylococcus* species, and a device for detecting *Streptococcus* species, which are selected depending on the detection target bacteria. The detection device may be selected and used depending on the bacteria as the detection target. When additional bacteriolysis enzymes are added, they are selected depending on the detection target bacteria.

According to another embodiment, the bacterial detection kit may contain the bacteriolysis aid according to the present invention and, as the lateral flow type immunochromatographic detection devices according to the present invention, a device for detecting *Escherichia* species, a device for detecting *Staphylococcus* species, and a device for detecting *Streptococcus* species, which three detection devices may be used at the same time. The bacteriolysis enzymes may be attached to the detection devices in advance or may be added upon use.

The device for detecting *Escherichia* species contains a labeling antibody and a capture antibody for *Escherichia* species detection, which are attached to the labeling antibody-attached member 1 and the membrane carrier for chromatographic development 2, respectively. The device may also contain the bacteriolysis enzyme-attached member 4, to which lysozyme is attached.

The device for detecting *Staphylococcus* species contains a labeling antibody and a capture antibody for *Staphylococcus* species detection, which are attached to the labeling antibody-attached member 1 and the membrane carrier for chromatographic development 2, respectively. The device may also contain the bacteriolysis enzyme-attached member 4, to which lysostaphin is attached.

The device for detecting *Streptococcus* species contains a labeling antibody and a capture antibody for *Streptococcus* species detection, which are attached to the labeling antibody-attached member 1 and the membrane carrier for chromatographic development 2, respectively. The device may also contain the bacteriolysis enzyme-attached member 4, to which at least one bacteriolysis enzyme selected from the group consisting of lysozyme, acetyl glucosaminidase and endopeptidase is attached.

According to another embodiment, the bacterial detection kit may contain the bacteriolysis aid according to the present invention and a device for simultaneously detecting three species, i.e., *Escherichia* species, *Staphylococcus* species, and *Streptococcus* species. The detection device for simultaneous detection of the three species is configured to include a labeling antibody for detection of *Escherichia* species, a labeling antibody for detection of *Staphylococcus* species, and a labeling antibody for detection of *Streptococcus* species, as well as a capture antibody for detection of *Escherichia* species, a capture antibody for detection of *Staphylococcus* species, and a capture antibody for detection of *Streptococcus* species. The bacteriolysis enzyme may be attached to one or more bacteriolysis enzyme-attached members 4 of the detection device in advance, or may be added externally as bacteriolysis enzymes upon use.

More specifically, the detection device for simultaneous detection of the three species may contain a single labeling antibody-attached member 1, to which the labeling antibody for detection of *Escherichia* species, the labeling antibody for detection of *Staphylococcus* species, and the labeling antibody for detection of *Streptococcus* species are attached together. Alternatively, the detection device for simultaneous detection of the three species may contain two or more labeling antibody-attached members 1, to each of which the labeling antibody for detection of *Escherichia* species, the labeling antibody for detection of *Staphylococcus* species, and/or the labeling antibody for detection of *Streptococcus* species are attached separately or together.

Still more specifically, the detection device for simultaneous detection of the three species may contain a membrane carrier for chromatographic development 2, to which the capture antibody for detection of *Escherichia* species, the capture antibody for detection of *Staphylococcus* species, and the capture antibody for detection of *Streptococcus* species are attached at two or more different positions or at the same position. For example, the capture antibody for detection of *Staphylococcus* species and the capture antibody for detection of *Streptococcus* species may be attached at the same position. In this case, when the labeling antibody-antigen complex captured at this attachment position is detected, it can be determined that Gram-positive bacteria were detected.

The positions to which the three capture antibodies are attached may be arranged on the membrane carrier for chromatographic development 2 side by side in the direction perpendicular to the specimen flow, or they may be separated in the direction of the sample flow. The order of the positions to which the three capture antibodies are attached is not limited, but as an example, they can be arranged in the following order from upstream: the capture antibody for detection of *Staphylococcus* species, the capture antibody for detection of *Streptococcus* species, and the capture antibody for detection of *Escherichia* species. As another example, the detection device for simultaneous detection of the three species may contain two or more (i.e., two or three) membrane carriers for chromatographic development 2, to each of which the capture antibody for detection of *Escherichia* species, the capture antibody for detection of *Staphylococcus* species, and/or the capture antibody for detection of *Streptococcus* species are attached.

EXAMPLES

The present invention will be described in more detail in the following examples, but these examples are only shown for convenience of explanation, and the present invention is not limited to these examples in any sense.

Example 1: Effects of pH and Electrical Conductivity on the Detection of *Staphylococcus Aureus, Escherichia Coli*, and *Streptococcus uberis* by Immunochromatography (1) Production of an Immunochromatographic Detection Device for Detecting *Staphylococcus aureus* in Milk An immunochromatographic detection device was produced according to the following procedure.

(a) Production of Monoclonal Antibodies Against Ribosome Protein L7/L12

*Staphylococcus aureus* ribosomal protein L7/L12 monoclonal antibodies were used as the antibody to be labeled with gold colloids. Specifically, according to the method described in Example 5 of WO2000/006603 A, the L7/L12 ribosome protein of *Staphylococcus aureus* was obtained and used for production of monoclonal antibodies. The monoclonal antibodies selected are a combination of two clones (SA-1 and SA-2) that can simultaneously bind to different sites of the L7/L12 ribosomal protein above.

(b) Gold Colloid Label-Impregnated Member

BB International gold colloid solution (60 nm particle size) in a volume of 0.9 mL was mixed with 0.1 M potassium phosphate pH 7.0, and then combined with 100 μg/mL of monoclonal antibody SA-2 to be labeled with gold colloids and allowed to stand for 10 minutes at room temperature, to allow this antibody to bind to the surface of the gold colloidal particles. A 10% aqueous solution of bovine serum albumin (BSA) was then added so that the final concentration in the gold colloid solution was 1% to block the remaining surface of the gold colloidal particles with BSA, whereby a solution of gold colloid-labeled monoclonal antibody SA-2 (hereafter referred to as the "gold colloid-labeled antibody") was prepared. This solution was centrifuged (at 15000×rpm for 5 minutes) to precipitate the gold colloid-labeled antibody, and the supernatant solution was removed to obtain the gold colloid-labeled antibody. This gold colloid-labeled antibody was then suspended in 20 mM tris hydrochloric acid buffer solution (pH 8.2) containing 0.25% BSA, 2.5% sucrose, and 35 mM NaCl to thereby obtain a gold colloid-labeled antibody solution. A strip of glass fiber pad of 5 mm×300 mm was impregnated with 1 mL of the gold colloid-labeled antibody solution and dried under reduced pressure at room temperature to prepare a gold colloid-labeled antibody-impregnated member (hereinafter referred to as gold colloid-labeled antibody-impregnated member 1) as the labeling antibody-attached member 1.

(c) Capture Site of Complex Between Antigen and Gold Colloid-Labeled Antibody

A nitrocellulose membrane with a width of 25 mm and a length of 300 mm was prepared as the membrane carrier for chromatographic development 2 (second part) of chromatographic media. A solution containing 1.5 mg/mL of monoclonal antibody SA-1 was applied in a line at 1 μL/cm at a position of 10 mm from the end of the chromatographic development start point on the membrane carrier for chromatographic development 2. The membrane carrier was dried at 50° C. for 30 minutes, then soaked in a 0.5% sucrose solution for 30 minutes, and dried at room temperature overnight, whereby the capture site 3 for the complex formed of the *Staphylococcus aureus* ribosome protein L7/L12 antigen and the gold colloid-labeled antibody.

(d) Bacteriolysis Enzyme-Attached Member

Recombinant lysostaphin manufactured by Fujifilm Wako Pure Chemical Corporation was dissolved in 20 mM sodium acetate buffer (pH 4.5) to a concentration of 100 μg/mL. A strip of glass fiber pad of 5 mm×300 mm was impregnated with 1 mL of the enzyme solution and air dried at room temperature to prepare a bacteriolysis enzyme-attached member 4.

(e) Production of an Immunochromatographic Device

A cross-sectional view of the immunochromatographic detection system is shown in FIG. 1.

In addition to the gold colloid-labeled antibody-impregnated member 1 and the membrane carrier for chromatographic development 2 explained above, a sample contact member 5, a filter member 6, and an absorption member 7 were layered on a base material 8, and cut into 5 mm in width, to thereby produce an immunochromatographic detection device 10. A 20-mm GF/DVA (GE Healthcare Biosciences: filter member made of glass fiber with a thickness of 776 μm and a retained particle size of 3.5 μm) was used as the sample contact member 5. This member also serves as a member for removing fat globules. A 15-mm GF/AVA (GE Healthcare Biosciences: filter member made of glass fiber with a thickness of 299 μm and a retained particle size of 1.7 μm) was used as the filter member 6, filter paper was used as the absorbent member 7, and a 254-μm thick polystyrene film with adhesive material to attach other members was used as the base material 8.

(2) Production of an Immunochromatographic Detection Device for Detecting *Escherichia coli* in Milk An immunochromatographic detection device was produced according to the following procedure.

(a) Production of Monoclonal Antibodies Against Ribosome Protein L7/L12

*Escherichia coli* ribosomal protein L7/L12 monoclonal antibodies were used as the antibody to be labeled with gold colloids. Specifically, according to the method described in Example 5 of WO2000/006603 A, the L7/L12 ribosome protein of *Escherichia coli* was obtained and used for production of monoclonal antibodies. The monoclonal antibodies selected are a combination of two clones (EC-1 and EC-2) that can simultaneously bind to different sites of the L7/L12 ribosomal protein of the above *Escherichia coli* and another *Escherichia* species.

(b) Gold Colloid Label-Impregnated Member

BB International gold colloid solution (60 nm particle size) in a volume of 0.9 mL was mixed with 0.1 M potassium phosphate pH 7.0, and then combined with 100 μg/mL of monoclonal antibody EC-2 to be labeled with gold colloids and allowed to stand for 10 minutes at room temperature, to allow this antibody to bind to the surface of the gold colloidal particles. A 10% aqueous solution of bovine serum albumin (BSA) was then added so that the final concentration in the gold colloid solution was 1% to block the remaining surface of the gold colloidal particles with BSA, whereby a solution of gold colloid-labeled monoclonal antibody EC-2 (hereafter referred to as the "gold colloid-labeled antibody") was prepared. This solution was centrifuged (at 15000×rpm for 5 minutes) to precipitate the gold colloid-labeled antibody, and the supernatant solution was removed to obtain the gold colloid-labeled antibody. This gold colloid-labeled antibody was then suspended in 20 mM tris hydrochloric acid buffer solution (pH 8.2) containing 0.25% BSA, 2.5% sucrose, and 35 mM NaCl to thereby obtain a gold colloid-labeled antibody solution. A strip of glass fiber pad of 10 mm×300 mm was impregnated with 2 mL of the gold colloid-labeled antibody solution and dried under reduced pressure at room temperature to prepare a gold colloid-labeled antibody-impregnated member (hereinafter referred to as gold colloid-labeled antibody-impregnated member 1) as the labeling antibody-attached member 1.

(c) Capture Site of Complex Between Antigen and Gold Colloid-Labeled Antibody

A nitrocellulose membrane with a width of 25 mm and a length of 300 mm was prepared as the membrane carrier for chromatographic development 2 of chromatographic media. A solution containing 1.5 mg/mL of monoclonal antibody EC-1 was applied in a line at 1 μL/cm at a position of 10 mm from the end of the chromatographic development start point on the membrane carrier for chromatographic development 2. The membrane carrier was dried at 50° C. for 30 minutes, then soaked in a 0.5% sucrose solution for 30 minutes, and dried at room temperature overnight, whereby the capture site 3 for the complex formed of the *Escherichia coli* ribosome protein L7/L12 antigen and the gold colloid-labeled antibody.

(d) Bacteriolysis Enzyme-Attached Member

Lysozyme manufactured by Creative Enzymes was dissolved in 20 mM tris hydrochloric acid buffer solution (pH 8.0) to a concentration of 50 mg/mL. A strip of glass fiber pad of 5 mm×300 mm was impregnated with 1 mL of the enzyme solution and air dried at room temperature to prepare a bacteriolysis enzyme-attached member 4.

(e) Production of an Immunochromatographic Device

A cross-sectional view of the immunochromatographic detection system is shown in FIG. 1.

In addition to the gold colloid-labeled antibody-impregnated member 1 and the membrane carrier for chromatographic development 2 explained above, a sample contact member 5, a filter member 6, and an absorption member 7 were layered on a base material 8, and cut into 5 mm in width, to thereby produce an immunochromatographic detection device 10. A 20-mm GF/DVA (GE Healthcare Biosciences: filter member made of glass fiber with a thickness of 776 μm and a retained particle size of 3.5 μm) was used as the sample contact member 5. This member also serves as a member for removing fat globules. A 15-mm GF/AVA (GE Healthcare Biosciences: filter member made of glass fiber with a thickness of 299 μm and a retained particle size of 1.7 μm) was used as the filter member 6, filter paper was used as the absorbent member 7, and a 254-μm thick polystyrene film with adhesive material to attach other members was used as the base material 8.

(3) Production of an Immunochromatographic Detection Device for Detecting *Streptococcus* Species in Milk An immunochromatographic detection device was produced according to the following procedure.

(a) Production of Monoclonal Antibodies Against Ribosome Protein L7/L12

According to the method described in Example 5 of WO2000/06603 A, the L7/L12 ribosome protein of *Streptococcus uberis* was obtained and used for production of monoclonal antibodies. The monoclonal antibodies selected are a combination of two clones that can simultaneously bind to different sites of the L7/L12 ribosomal protein above.

(b) Gold Colloid Label-Impregnated Member

BB International gold colloid solution (60 nm particle size) in a volume of 0.9 mL was mixed with 0.1 M potassium phosphate pH 7.0, and then combined with 100 μg/mL of monoclonal antibody SU-2 to be labeled with gold colloids and allowed to stand for 10 minutes at room temperature, to allow this antibody to bind to the surface of the gold colloidal particles. A 10% aqueous solution of bovine serum albumin (BSA) was then added so that the final concentration in the gold colloid solution was 1% to block the remaining surface of the gold colloidal particles with BSA, whereby a solution of gold colloid-labeled monoclonal antibody SU-2 (hereafter referred to as the "gold colloid-labeled antibody") was prepared. This solution was centrifuged (at 15000×rpm for 5 minutes) to precipitate the gold colloid-labeled antibody, and the supernatant solution was removed to obtain the gold colloid-labeled antibody. This gold colloid-labeled antibody was then suspended in 20 mM tris hydrochloric acid buffer solution (pH 8.2) containing 0.25% BSA, 2.5% sucrose, and 35 mM NaCl to thereby obtain a gold colloid-labeled antibody solution. A strip of glass fiber pad of 10 mm×300 mm was impregnated with 2 mL of the gold colloid-labeled antibody solution and dried under reduced pressure at room temperature to prepare a gold colloid-labeled antibody-impregnated member (hereinafter referred to as gold colloid-labeled antibody-impregnated member 1) as the labeling antibody-attached member 1.

(c) Capture Site of Complex Between Antigen and Gold Colloid-Labeled Antibody

A nitrocellulose membrane with a width of 25 mm and a length of 300 mm was prepared as the membrane carrier for chromatographic development 2 of chromatographic media. A solution containing 1.5 mg/mL of monoclonal antibody SU-1 was applied in a line at 1 μL/cm at a position of 10 mm from the end of the chromatographic development start point on the membrane carrier for chromatographic development 2. The membrane carrier was dried at 50° C. for 30 minutes, then soaked in a 0.5% sucrose solution for 30 minutes, and dried at room temperature overnight, whereby the capture site 3 for the complex formed of the *Streptococcus uberis* ribosome protein L7/L12 antigen and the gold colloid-labeled antibody.

(d) Bacteriolysis Enzyme-Attached Member

Labiase manufactured by Cosmo Bio Co., Ltd. was dissolved in 20 mM tris hydrochloric acid buffer solution (pH 8.0) to a concentration of 30 μg/mL. A strip of glass fiber pad of 5 mm×300 mm was impregnated with 1 mL of the enzyme solution and air dried at room temperature to prepare a bacteriolysis enzyme-attached member 4.

(e) Production of an Immunochromatographic Device

A cross-sectional view of the immunochromatographic detection system is shown in FIG. 1.

In addition to the gold colloid-labeled antibody-impregnated member 1 and the membrane carrier for chromatographic development 2 explained above, a sample contact member 5, a filter member 6, and an absorption member 7 were layered on a base material 8, and cut into 5 mm in width, to thereby produce an immunochromatographic detection device 10. A 20-mm GF/DVA (GE Healthcare Biosciences: filter member made of glass fiber with a thickness of 776 μm and a retained particle size of 3.5 μm) was used as the sample contact member 5. This member also serves as a member for removing fat globules. A 15-mm GF/AVA (GE Healthcare Biosciences: filter member made of glass fiber with a thickness of 299 μm and a retained particle size of 1.7 μm) was used as the filter member 6, filter paper was used as the absorbent member 7, and a 254-μm thick polystyrene film with adhesive material to attach other members was used as the base material 8.

(4) Test Measurement of Milk with the Immunochromatographic Detection Devices

The measurement of milk using the immunochromatography detection devices was performed as follows: 500 μL of each bacteriolysis aid solution listed in Table 1 was dispensed into microtubes each containing one 5 mm×5 mm piece of bacteriolysis enzyme-attached member 4 (lysostaphin impregnated) for detecting *Staphylococcus aureus*. 300 μL of milk with a final *Staphylococcus aureus* concentration of $2×10^5$ (cfu/mL) was put into each microtube and treated for 30 minutes at room temperature. The pH and electrical conductivity of the bacteriolysis aid were measured using a compact pH meter LAQUA twin and a compact electrical conductivity meter LAQUAtwin (HORIBA), respectively. The milk used was a commercial product (pH 6.4, electrical conductivity 4.0 mS/cm). After measuring the pH and electrical conductivity of the mixture solution, a portion of the sample contact member 5 of the immunochromatographic detection device 10 for detection of *Staphylococcus aureus* in milk was immersed and allowed to stand at room temperature for 30 minutes to develop, and the reddish purple line was visually determined.

In addition, 500 μL of each bacteriolysis aid listed in Table 1 was dispensed into microtubes each containing one 5 mm×5 mm piece of bacteriolysis enzyme-attached member 4 (lysozyme attached) for detecting *Escherichia coli*. 300 L of milk with a final *Escherichia coli* concentration of $2×10^5$ (cfu/mL) was put into each microtube and treated for 30 minutes at room temperature. The milk used was a commercial product (pH 6.4, electrical conductivity 4.0 mS/cm). A portion of the sample contact member 5 of the immunochromatographic detection device 10 for detection of *Escherichia coli* in milk was immersed and allowed to stand at room temperature for 30 minutes to develop, and the reddish purple line was visually determined.

Likewise, 500 μL of each bacteriolysis aid listed in Table 1 was dispensed into microtubes each containing one 5 mm×5 mm piece of bacteriolysis enzyme-attached member 4 (lysozyme attached) for detecting *Streptococcus* species. 300 μL of milk with a final *Streptococcus uberis* concentration of $2×10^5$ (cfu/mL) was put into each microtube and treated for 30 minutes at room temperature. The milk used was a commercial product (pH 6.4, electrical conductivity 4.0 mS/cm). A portion of the sample contact member 5 of the immunochromatographic detection device 10 for detection of *Streptococcus* species in milk was immersed and allowed to stand at room temperature for 30 minutes to develop, and the reddish purple line was visually determined.

The evaluation results are shown in Table 2, in which visually positives are indicated as + and visually negatives as –, along with the measurement results of pH and electrical conductivity after mixing milk with various bacteriolysis aids. Table 2 shows that all three bacteria were detectable under the conditions that lysostaphin, lysozyme, and labiase were used as enzymes, and that the pH was within from 6.0 to 7.0 and the electrical conductivity was from 2.5 to 8.5 after mixing milk with various bacteriolysis aids.

TABLE 1

| | | Nonionic surfactant | | | Electrical |
| --- | --- | --- | --- | --- | --- |
| Condition | Product name | Conc. [%] | pH | | conductivity [mS/cm] |
| 1 | Triton ™X-100 | 3 | 6.6 | | 3 |
| 2 | Triton ™X-100 | 3 | 6.0 | | 2 |
| 3 | Triton ™X-100 | 3 | 6.0 | | 8 |
| 4 | Triton ™X-100 | 3 | 7.0 | | 2 |
| 5 | Triton ™X-100 | 3 | 7.0 | | 8 |
| 6 | Tween ®20 | 1.6 | 7.4 | | 6 |
| 7 | Triton ™X-100 | 1.8 | 7.4 | | 30 |
| 8 | Triton ™X-100/ Tween ®20 | 1.8/1.2 | 6.3 | | 12 |
| 9 | Triton ™X-100/ Tween ®20 | 1.2/0.9 | 6.9 | | 17 |
| 10 | Triton ™X-100 | 3 | 6.0 | | 1 |
| 11 | Triton ™X-100 | 3 | 7.0 | | 1 |
| 12 | Triton ™X-100 | 3 | 5.6 | | 8 |
| 13 | Triton ™X-100 | 3 | 5.6 | | 8 |

TABLE 2

| | | Nonionic surfactant | | | | |
| --- | --- | --- | --- | --- | --- | --- |
| | | Conc. after Mixing Sample with | pH after Mixing | Electrical conductivity after Mixing Sample with | Determination results by Kit | |
| Condition | Product name | Bacteriolysis aid [%] | Sample with Bacteriolysis aid | Bacteriolysis aid [mS/cm] | *Staphylococous aureus* | *Escherichia coli* | *Streptococcus uberis* |
| 1 | Triton ™ X-100 | 1.88 | 6.6 | 3.6 | + | + | + |
| 2 | Triton ™ X-100 | 1.88 | 6.0 | 2.8 | + | + | + |
| 3 | Triton ™ X-100 | 1.88 | 6.0 | 6.5 | + | + | + |
| 4 | Triton ™ X-100 | 1.88 | 7.0 | 2.8 | + | + | + |
| 5 | Triton ™ X-100 | 1.88 | 7.0 | 6.5 | + | + | + |
| 6 | Tween ® 20 | 1.00 | 7.4 | 5.3 | + | – | – |
| 7 | Triton ™ X-100 | 1.13 | 7.4 | 20 | – | + | – |
| 8 | Triton ™ X-100/ Tween@20 | 1.13/0.75 | 6.3 | 9.3 | – | – | + |
| 9 | Triton ™ X-100/ Tween@20 | 0.75/0.56 | 6.9 | 12 | + | – | + |
| 10 | Triton ™ X-100 | 1.88 | 6.0 | 2.1 | + | – | + |
| 11 | Triton ™ X-100 | 1.88 | 7.0 | 2.1 | + | – | – |
| 12 | Triton ™ X-100 | 1.88 | 5.6 | 2.8 | – | – | – |
| 13 | Triton ™ X-100 | 1.88 | 5.6 | 6.5 | – | – | + |

Example 2: Effect of Nonionic Surfactants on Detection of *Staphylococcus aureus, Escherichia Coli*, and *Streptococcus uberis* by Immunochromatography (1) The Measurement of Milk Using the Immunochromatographic Detection Devices was Carried Out in Accordance with the Procedure Described in Example 1.

Like in Example 1, the evaluation results using the immunochromatographic detection device for detection of each species are shown in Table 4, in which visually positives are indicated as + and visually negatives as −, along with the measurement results of pH and electrical conductivity after mixing milk with various bacteriolysis aids. Table 4 shows that all three bacteria were detectable under the conditions that lysostaphin, lysozyme, and labiase were used as enzymes, that the nonionic surfactant used in the bacteriolysis aid was polyoxyethylene alkyl phenyl ether and the nonionic surfactant concentration after mixing with milk was 1.25% to 3.13%, and that the pH was from 6.0 to 7.0 and the electrical conductivity was from 2.5 to 8.5 after mixing milk with various bacteriolysis aids. The bacteriolysis aids used was listed in Table 3.

TABLE 3

| | Nonionic surfactant | | | | Electrical |
|---|---|---|---|---|---|
| Condition | Type | Product name | Conc. [%] | pH | conductivity [mS/cm] |
| 1 | Polyoxyethylene alkylphenyl ether | Triton ™X-100 | 3 | 6.6 | 3 |
| 14 | Polyoxyethylene alkylphenyl ether | Triton ™X-100 | 5 | 6.6 | 3 |
| 15 | Polyoxyethylene alkylphenyl ether | Triton ™X-100 | 4 | 6.6 | 3 |
| 16 | Polyoxyethylene alkylphenyl ether | Triton ™X-100 | 2 | 6.6 | 3 |
| 17 | Polyoxyethylene alkylphenyl ether | Triton ™X-114 | 3 | 6.6 | 3 |
| 18 | Polyoxyethylene alkylphenyl ether | Nonidet ™ P40 Substitute | 3 | 6.6 | 3 |
| 19 | Polyoxyethylene alkylphenyl ether | Triton ™X-100 | 1 | 6.6 | 3 |
| 20 | Polyoxyethylene alkylphenyl ether Sorbitan fatty acid ester | Tween ®20 | 3 | 6.6 | 3 |

TABLE 4

| | Nonionic surfactant | | | | Electrical conductivity | Determination results by Kit | | |
|---|---|---|---|---|---|---|---|---|
| Condition | Type | Product name | Conc. after Mixing Sample with Bacteriolysis aki | pH after Mixing Sample with Bacteriolysis aid | after Mixing Sample with Bacteriolysis aid [mS/cm] | *Staphylococcus aureus* | *Escherichia coli* | *Streptococcus ubens* |
| 1 | Polyoxyethylene alkyphenyl ether | Triton ™ X-100 | 1.88 | 6.6 | 3.6 | + | + | + |
| 14 | Polyoxyethylene alkyphenyl ether | Triton ™ X-100 | 3.13 | 6.6 | 3.6 | + | + | + |
| 15 | Polyoxyethylene alkyphenyl ether | Triton ™ X-100 | 2.5 | 6.6 | 3.6 | + | + | + |
| 16 | Polyoxyethylene alkyphenyl ether | Triton ™ X-100 | 1.25 | 6.6 | 3.6 | + | + | + |
| 17 | Polyoxyethylene alkyphenyl ether | Triton ™ X-114 | 1.88 | 6.6 | 3.6 | + | + | + |
| 18 | Polyoxyethylene alkyphenyl ether | Nonidet ™ P40 Substitute | 1.88 | 6.6 | 3.6 | + | + | + |
| 19 | Polyoxyethylene alkyphenyl ether | Triton ™ X-100 | 0.63 | 6.6 | 3.6 | + | − | + |
| 20 | Polyoxyethylene alkyphenyl ether Sorbitan fatty acid ester | Tween ® 20 | 1.88 | 6.6 | 3.6 | + | − | − |

Example 2-1: Physical Properties of Nonionic Surfactants and their Effects in the Detection of *Staphylococcus aureus, Escherichia Coli*, and *Streptococcus uberis* by Immunochromatography (1) Production of immunochromatographic devices were carried out in accordance with the procedure described in Example 1. The bacteriolysis aids used for the test are listed in Table 4-1.

(2) The immunochromatographic detection devices for the detection of *Staphylococcus aureus, Escherichia species, Streptococcus* species detection were produced in accordance with the procedures described in Examples 1 (1), (2), and (3), respectively. The measurement of milk using the immunochromatographic detection devices was carried out in accordance with the procedure described in Example 1 (4), using milk samples with final *Staphylococcus aureus, Escherichia species*, or *Streptococcus* species concentrations of $4\times10^5$ and $2\times10^5$ (cfu/mL).

Like in Example 1, the evaluation results using the immunochromatographic detection device for detection of each species are shown in Table 4-2, in which visually positives are indicated as + and visually negatives as −, along with the measurement results of pH and electrical conductivity after mixing milk with various bacteriolysis aids.

TABLE 4-1

| | Nonionic surfactant | | | | | Electrical |
|---|---|---|---|---|---|---|
| Condition | Product name | Repeat Number of Polyoxyethylene | HLB value | Conc. [%] | pH | conductivity [mS/cm] |
| 1 | Triton ™ X-100 | 9.5 | 13.5 | 3 | 6.6 | 3 |
| 28 | Nonidet ™ P40 Substitute | 9 | 13.5 | 3 | 6.6 | 3 |
| 29 | Triton ™ X-100 reduced | 9.4 | 13.5 | 3 | 6.6 | 3 |
| 30 | Genapol ® X-080 | 8.6 | 13 | 3 | 6.6 | 3 |
| 31 | TERGITOL ™ 15-S-9 | 9 | 13.3 | 3 | 6.6 | 3 |
| 32 | TERGITOL ™ TMN-100X | 9 | 14.1 | 3 | 6.6 | 3 |
| 33 | TERGITOL ™ TMN-6 | 8 | 13.1 | 3 | 6.6 | 3 |
| 17 | TritonX ™ -114 | 7.5 | 12.4 | 3 | 6.6 | 3 |
| 34 | TERGITOL ™ 15-S-7 | 7 | 12.1 | 3 | 6.6 | 3 |
| 35 | TERGITOL TMN-10 | 11 | 14.4 | 3 | 6.6 | 3 |
| 36 | TERGITOL ™ 15-S-12 | 12 | 14.5 | 3 | 6.6 | 3 |
| 37 | TERGITOL ™ 15-S-15 | 15 | 15.4 | 3 | 6.6 | 3 |
| 38 | Briji ® 58 | 20 | 16 | 3 | 6.6 | 3 |
| 39 | Briji ® 35 (L23) | 23 | 16.9 | 3 | 6.6 | 3 |
| 40 | TERGITOL 15-S-30 | 31 | 17.4 | 3 | 6.6 | 3 |
| 41 | TERGITOL 15-S-40 | 41 | 18 | 3 | 6.6 | 3 |

TABLE 4-2

| | Nonionic surfactant | | | | pH after | Electrical |
|---|---|---|---|---|---|---|
| Condition | Product name | Repeat number of polyoxyethylene | HLB value | Conc. after Mixing Sample with Bacteriolysis aid [%] | Mixing Sample with Bacteriatysis aid | conductivity after Mixing Sample with Bacteriolysis aid [mS/cm] |
| 1 | Triton ™ X-100 | 9.5 | 13.5 | 1.88 | 6.6 | 3.6 |
| 28 | Nonidet ™ P40 | 9 | 13.5 | 1.88 | 6.6 | 3.6 |
| 29 | Triton ™ X-100 reduced | 9.4 | 13.5 | 1.88 | 6.6 | 3.6 |
| 30 | Genapol ® X-080 | 8.6 | 13 | 1.88 | 6.6 | 3.6 |
| 31 | TERGITOL ™ 15-S-S | 9 | 13.3 | 1.88 | 6.6 | 3.6 |
| 32 | TERGITOL ™ TMN-100X | 9 | 14.1 | 1.88 | 6.6 | 3.6 |
| 33 | TERGITOL ™ TMN-6 | 8 | 13.1 | 1.88 | 6.6 | 3.6 |
| 17 | TritonX ™ -114 | 7.5 | 12.4 | 1.88 | 6.6 | 3.6 |
| 34 | TERGITOL ™ 15-5-7 | 7 | 12.1 | 1.88 | 6.6 | 3.6 |
| 35 | TERGITOLT ™ TMN-10 | 11 | 14.4 | 1.88 | 6.6 | 3.6 |
| 36 | TERGITOL ™ 15-S-12 | 12 | 14.5 | 1 88 | 6.6 | 3.6 |
| 37 | TERGITOL ™ 15-S-15 | 15 | 15.4 | 1.88 | 6.6 | 3.6 |
| 36 | Bra ® 58 | 20 | 16 | 1.88 | 6.6 | 3.6 |
| 39 | Brij ® 35 (L23) | 23 | 16.9 | 1.88 | 6.6 | 3.6 |
| 40 | TERGITOL ® 15-5-30 | 31 | 17.4 | 1.88 | 6.6 | 3.6 |
| 41 | TERGITOL ® 15-5-40 | 41 | 18 | 1.88 | 6.6 | 3.6 |

TABLE 4-2-continued

| | Determination results by Kit | | | | | |
|---|---|---|---|---|---|---|
| | *Staphylococcus aureus* | | *Escherichia coli* | | *Streptococcus uberis* | |
| Condition | 4 × $10^5$ [CFU/mL] | 2 × $10^5$ [CFU/mL] | 4 × $10^5$ [CFU/mL] | 2 × $10^5$ [CFU/mL] | 4 × $10^5$ [CFU/mL] | 4 × $10^5$ [CFU/mL] |
| 1 | + | + | + | + | + | + |
| 28 | + | + | + | + | + | + |
| 29 | + | + | + | + | + | + |
| 30 | + | + | + | + | + | + |
| 31 | + | + | + | + | + | + |
| 32 | + | + | + | + | + | + |
| 33 | + | + | + | + | + | + |
| 17 | + | + | + | + | + | + |
| 34 | + | − | + | − | + | − |
| 35 | + | − | + | − | + | − |
| 36 | − | − | − | − | − | − |
| 37 | − | − | − | − | − | − |
| 36 | − | − | − | − | − | − |
| 39 | − | − | − | − | − | − |
| 40 | − | − | − | − | − | − |
| 41 | − | − | − | − | − | − |

Table 4-2 shows that all three bacteria each at a concentration of 4×$10^5$ [CFU/mL] were detectable under the conditions that lysostaphin, lysozyme, and labiase were used as enzymes, that the pH was within the range of from 6.0 to 7.0 and the electrical conductivity was from 2.5 to 8.5 after mixing milk with various bacteriolysis aids, that the nonionic surfactant used in the bacteriolysis aid had a polyoxyethylene chain with a number of repetitions of from 7 to 11 and an HLB value of from 12.0 or more but less than 14.5, and that the nonionic surfactant concentration was 1.88%. This table also shows that all three bacteria each at a concentration of 2×$10^5$ [CFU/mL] were detectable under the conditions that the nonionic surfactant used in the bacteriolysis aid had a polyoxyethylene chain with a number of repetitions of from 7.5 to 10 and an HLB value of from 12.4 to 14.1, and that the nonionic surfactant concentration was 1.88%.

Example 3: Effects of Anionic Surfactants and Zwitterionic Surfactants and Gamma Globulin on the Detection of *Staphylococcus aureus, Escherichia Coli*, and *Streptococcus uberis* by Immunochromatography (1) Test Measurement of Milk with the Immunochromatographic Detection Devices The measurement of milk using the immunochromatography detection devices was performed as follows: 500 μL of each bacteriolysis aid solution listed in Table 5 was dispensed into microtubes each containing one 5 mm×5 mm piece of bacteriolysis enzyme-attached member 4 (lysostaphin impregnated) for detecting *Staphylococcus aureus.* 300 μL of milk with a final *Staphylococcus aureus* concentration of 1×$10^5$ (cfu/mL) was put into each microtube and treated for 30 minutes at room temperature. The pH and electrical conductivity of the bacteriolysis aid were measured using a compact pH meter LAQUA twin and a compact electrical conductivity meter LAQUAtwin (HORIBA), respectively. The milk used was a commercial product (pH 6.4, electrical conductivity 4.0 mS/cm). After measuring the pH and electrical conductivity of the mixture solution, a portion of the sample contact member 5 of the immunochromatographic detection device 10 for detection of *Staphylococcus aureus* in milk according to Example 1 was immersed and allowed to stand at room temperature for 30 minutes to develop, and the reddish purple line was visually determined.

In addition, 500 μL of each bacteriolysis aid listed in Table 5 was dispensed into microtubes each containing one 5 mm×5 mm piece of bacteriolysis enzyme-attached member 4 (lysozyme attached) for detecting *Escherichia coli.* 300 μL of milk with a final *Escherichia coli* concentration of 1×$10^5$ (cfu/mL) was put into each microtube and treated for 30 minutes at room temperature. The milk used was a commercial product (pH 6.4, electrical conductivity 4.0 mS/cm). A portion of the sample contact member 5 of the immunochromatographic detection device 10 for detection of *Escherichia coli* in milk according to Example 1 was immersed and allowed to stand at room temperature for 30 minutes to develop, and the reddish purple line was visually determined.

Likewise, 500 μL of each bacteriolysis aid listed in Table 5 was dispensed into microtubes each containing one 5 mm×5 mm piece of bacteriolysis enzyme-attached member 4 (lysozyme attached) for detecting *Streptococcus* species. 300 μL of milk with a final *Streptococcus uberis* concentration of 1×$10^5$ (cfu/mL) was put into each microtube and treated for 30 minutes at room temperature. The milk used was a commercial product (pH 6.4, electrical conductivity 4.0 mS/cm). A portion of the sample contact member 5 of the immunochromatographic detection device 10 for detection of *Streptococcus* species in milk according to Example 1 was immersed and allowed to stand at room temperature for 30 minutes to develop, and the reddish purple line was visually determined.

Like in Example 1, the evaluation results using the immunochromatographic kit 10 for detection of each species are shown in Table 6, in which visually positives are indicated as + and visually negatives as −, along with the measurement results of pH and electrical conductivity after mixing milk with various bacteriolysis aids. Table 6 shows that all three bacteria each at a concentration of 1×$10^5$ were detectable under the conditions that lysostaphin, lysozyme, and labiase were used as enzymes, that the nonionic surfactant used in the bacteriolysis aid was polyoxyethylene alkyl phenyl ether and the nonionic surfactant concentration after mixing with milk was from 1.25% to 3.13%, that the pH was within the range of from 6.0 to 7.0 and the electrical conductivity was from 2.5 to 8.5 after mixing milk with various bacteriolysis aids, and that the concentration of anionic surfactant sodium dodecanoyl sarcosinate was 0.31%, the concentration of zwitterionic surfactant Zwittergent 3-12 was 0.09%, or the concentration of gamma globulin was 6.25 μg/mL.

TABLE 5

| Condition | Triton ™ X-100 Conc. [%] | Sodium dodecanoyl sarcosinate Conc. [%] | Zwittergent ® 3-12 Conc. [%] | Gamma globulin Conc. [ug/mL] | pH | Electrical conductivity [mS/cm] |
|---|---|---|---|---|---|---|
| 1 | 3 | 0 | 0 | 0 | 6.6 | 3 |
| 21 | 3 | 0.5 | 0.15 | 10 | 6.6 | 3 |

TABLE 6

| Condition | Conc. [%] after Mixing Sample with Bacteriolysis aid and Triton ™ X-100 | Conc. [%] after Mixing Sample with Bacteriolysis aid and Sodium dodecaneyl sarcosinate | Conc. [%] after Mixing Sample with Bacteriolysis aid and Zwittergent ® 3-12 | Conc. [ug/mL] after Mixing Sample with Bacteriolysis aid and Gamma globulin | pH | Electrical conductivity after Mixing Sample with Bacteriolysis aid [mS/cm] | Determination results by Kit *Staphylococcus aureus* | *Escherichia coli* | *Streptococcus uberis* |
|---|---|---|---|---|---|---|---|---|---|
| 2 | 1.88 | 0 | 0 | 0 | 6.6 | 3.6 | – | – | – |
| 21 | 1.88 | 0.31 | 0.09 | 6.25 | 6.6 | 3.6 | + | + | + |

In Examples 1 and 2, the presence or absence of $2\times10^5$ cfu/mL of each bacterial species could be determined under Condition 1, while in Example 3, $1\times10^5$ cfu/mL of bacteria could not be detected under the same Condition 1. However, the addition of an anionic surfactant and gamma globulin was shown to enable the detection of the same number of bacteria, indicating that the sensitivity of the immunochromatographic detection device was increased.

Example 4: Effect of the Mixing Ratio of the Bacteriolysis Aid and the Sample on Detection of *Staphylococcus aureus, Escherichia Coli*, and *Streptococcus uberis* by Immunochromatography (1) Test Measurement of Milk with the Immunochromatographic Detection Devices The measurement of milk using the immunochromatography detection devices was performed as follows: 500 μL or 300 μL of each bacteriolysis aid solution listed in Table 7 was dispensed into microtubes each containing one 5 mm×5 mm piece of bacteriolysis enzyme-attached member 4 (lysostaphin impregnated) for detecting *Staphylococcus aureus*. 300 μL of milk with a final *Staphylococcus aureus* concentration of $1\times10^5$ (cfu/mL) was put into each microtube and treated for 30 minutes at room temperature. The pH and electrical conductivity of the bacteriolysis aid were measured using a compact pH meter LAQUA twin and a compact electrical conductivity meter LAQUAtwin (HORIBA), respectively. The milk used was a commercial product (pH 6.4, electrical conductivity 4.0 mS/cm). After measuring the pH and electrical conductivity of the mixture solution, a portion of the sample contact member 5 of the immunochromatographic detection device 10 for detection of *Staphylococcus aureus* in milk according to Example 1 was immersed and allowed to stand at room temperature for 30 minutes to develop, and the reddish purple line was visually determined.

In addition, 500 μL or 300 μL of each bacteriolysis aid listed in Table 7 was dispensed into microtubes each containing one 5 mm×5 mm piece of bacteriolysis enzyme-attached member 4 (lysozyme attached) for detecting *Escherichia coli.* 300 μL of milk with a final *Escherichia coli* concentration of $1\times10^5$ (cfu/mL) was put into each microtube and treated for 30 minutes at room temperature. The milk used was a commercial product (pH 6.4, electrical conductivity 4.0 mS/cm). A portion of the sample contact member 5 of the immunochromatographic detection device 10 for detection of *Escherichia coli* in milk according to Example 1 was immersed and allowed to stand at room temperature for 30 minutes to develop, and the reddish purple line was visually Likewise, 500 μL or 300 μL of each bacteriolysis aid listed in Table 7 was dispensed into microtubes each containing one 5 mm×5 mm piece of bacteriolysis enzyme-attached member 4 (lysozyme attached) for detecting *Streptococcus* species. 300 μL of milk with a final *Streptococcus uberis* concentration of $1\times10^5$ (cfu/mL) was put into each microtube and treated for 30 minutes at room temperature. The milk used was a commercial product (pH 6.4, electrical conductivity 4.0 mS/cm). A portion of the sample contact member 5 of the immunochromatographic detection device 10 for detection of *Streptococcus* species in milk according to Example 1 was immersed and allowed to stand at room temperature for 30 minutes to develop, and the reddish purple line was visually determined.

Like in Example 1, the evaluation results using the immunochromatographic kit 10 for detection of each species are shown in Table 8, in which visually positives are indicated as + and visually negatives as –, along with the measurement results of pH and electrical conductivity after mixing milk with various bacteriolysis aids. Table 8 shows that all three bacteria each at a concentration of $1\times10^5$ cfu/mL were detectable under the conditions that lysostaphin, lysozyme, and labiase were used as enzymes, that the nonionic surfactant used in the bacteriolysis aid was polyoxyethylene alkyl phenyl ether and the nonionic surfactant concentration after mixing with milk was from 1.25% to 3.13%, that the pH was within the range of from 6.0 to 7.0 and the electrical conductivity was from 2.5 to 8.5 after mixing milk with various bacteriolysis aids, that the concentration of anionic surfactant sodium dodecanoyl sarcosinate was 0.31%, the concentration of zwitterionic surfactant Zwittergent 3-12 was 0.09%, or the concentration of gamma globulin was 6.25 μg/mL, and that the mixing ratio between the bacteriolysis aid and the sample was from 5:3 to 1:1.

gold colloid-labeled antibody was then suspended in 20 mM tris hydrochloric acid buffer solution (pH 8.2) containing 0.25% BSA, 2.5% sucrose, and 35 mM NaCl to thereby obtain a gold colloid-labeled antibody solution. A strip of glass fiber pad of 5 mm×300 mm was impregnated with 1 mL of the gold colloid-labeled antibody solution and dried

TABLE 7

| Condition | Triton ™ X-100 Conc. [%] | Sodium dodecanoyl sarcosinate Conc. [%] | Zwittergent ® 3-12 Conc. [%] | Gamma globulin Conc. [ug/mL] | pH | Electrical conductivity [mS/cm] | Bacteriolysis aid Volume [uL] |
|---|---|---|---|---|---|---|---|
| 21 | 3 | 0.5 | 0.15 | 10 | 6.6 | 3 | 500 |
| 22 | 3.75 | 0.625 | 0.188 | 12.5 | 6.6 | 3 | 300 |

TABLE 8

| Condition | Conc. [%] after Mixing Sample with Bacteriolysis aid and Triton ™ X-100 | Conc. [%] after Mixing Sample with Bacteriolysis aid and Sixlium dodecanoyl sarcosinate | Conc. [%] after Mixing Sample with Bacteriolysis aid and Zwittergent ® 2-12 | Conc. [ug/mL] after Mixing Sample with Bacteriolysis aid and Gamma globulin | pH | Electrical conductivity after Mixing Sample with Bacteriolysis aid [mS/cm] | Determination results by Kit | | |
|---|---|---|---|---|---|---|---|---|---|
| | | | | | | | *Staphylococcus aureus* | *Escherichia coli* | *Streptococcus ubers* |
| 21 | 1.98 | 0.31 | 0.09 | 6.25 | 6.6 | 3.6 | + | + | + |
| 22 | 1.88 | 0.31 | 0.09 | 6.25 | 6.6 | 3.6 | + | + | + |

Example 5: Simultaneous Detection of *Staphylococcus aureus, Escherichia Coli*, and *Streptococcus uberis* by Immunochromatography 1

(1) Production of an Immunochromatographic Detection Device for Detecting *Staphylococcus aureus* in Milk An immunochromatographic detection device was produced according to the following procedure.

(a) Production of Monoclonal Antibodies Against Ribosome Protein L7/L12

*Staphylococcus aureus* ribosomal protein L7/L12 monoclonal antibodies were used as the antibody to be labeled with gold colloids. Specifically, according to the method described in Example 5 of WO2000/006603 A, the L7/L12 ribosome protein of *Staphylococcus aureus* was obtained and used for production of monoclonal antibodies. The monoclonal antibodies selected are a combination of two clones (SA-1 and SA-2) that can simultaneously bind to different sites of the L7/L12 ribosomal protein above.

(b) Gold Colloid Label-Impregnated Member

BB International gold colloid solution (60 nm particle size) in a volume of 0.9 mL was mixed with 0.1 M potassium phosphate pH 7.0, and then combined with 100 μg/mL of monoclonal antibody SA-2 to be labeled with gold colloids and allowed to stand for 10 minutes at room temperature, to allow this antibody to bind to the surface of the gold colloidal particles. A 10% aqueous solution of bovine serum albumin (BSA) was then added so that the final concentration in the gold colloid solution was 1% to block the remaining surface of the gold colloidal particles with BSA, whereby a solution of gold colloid-labeled monoclonal antibody SA-2 (hereafter referred to as the "gold colloid-labeled antibody") was prepared. This solution was centrifuged (at 15000×rpm for 5 minutes) to precipitate the gold colloid-labeled antibody, and the supernatant solution was removed to obtain the gold colloid-labeled antibody. This under reduced pressure at room temperature to prepare a gold colloid-labeled antibody-impregnated member (hereinafter referred to as gold colloid-labeled antibody-impregnated member 1) as the labeling antibody-attached member 1.

(c) Capture Site of Complex Between Antigen and Gold Colloid-Labeled Antibody

A nitrocellulose membrane with a width of 25 mm and a length of 300 mm was prepared as the membrane carrier for chromatographic development 2 (second part) of chromatographic media. A solution containing 1.5 mg/mL of monoclonal antibody SA-1 was applied in a line at 1 μL/cm at a position of 10 mm from the end of the chromatographic development start point on the membrane carrier for chromatographic development 2. The membrane carrier was dried at 50° C. for 30 minutes, then soaked in a 0.5% sucrose solution for 30 minutes, and dried at room temperature overnight, whereby the capture site 3 for the complex formed of the *Staphylococcus aureus* ribosome protein L7/L12 antigen and the gold colloid-labeled antibody.

(d) Bacteriolysis Enzyme-Attached Member

Recombinant lysostaphin manufactured by Fujifilm Wako Pure Chemical Corporation was dissolved in 20 mM sodium acetate buffer (pH 4.5) to a concentration of 50 μg/mL. A strip of glass fiber pad of 10 mm×300 mm was impregnated with 2 mL of the enzyme solution and air dried at room temperature to prepare a bacteriolysis enzyme-attached member 4.

(e) Production of an Immunochromatographic Device

A cross-sectional view of the immunochromatographic detection system is shown in FIG. 2.

In addition to the gold colloid-labeled antibody-impregnated member 1, the bacteriolysis enzyme-attached member 4, and the membrane carrier for chromatographic development 2 explained above, a sample contact member 5, a filter member 6, and an absorption member 7 were layered on a base material 8, and cut into 5 mm in width, to thereby produce an immunochromatographic detection device 20. The bacteriolysis enzyme-attached member 4 was arranged at the upstream end of the sample contact member 5, between the base material 8 and the sample contact member. The gold colloid-labeled antibody-impregnated member 1 was arranged on the downstream side of the bacteriolysis enzyme-attached member 4, between the base material 8 and the bacteriolysis enzyme-attached member 4. A 26-mm GF/DVA (GE Healthcare Biosciences: filter member made of glass fiber with a thickness of 776 μm and a retained particle size of 3.5 μm) was used as the sample contact member 5. This member also serves as a member for removing fat globules. A 15-mm GF/AVA (GE Healthcare Biosciences: filter member made of glass fiber with a thickness of 299 μm and a retained particle size of 1.7 μm) was used as the filter member 6, filter paper was used as the absorbent member 7, and a 254-μm thick polystyrene film with adhesive material to attach other members was used as the base material 8.

(2) Production of an Immunochromatographic Detection Device for Detecting *Escherichia Coli* in Milk An immunochromatographic detection device was produced according to the following procedure.

(1) Production of an Immunochromatographic Detection Device for Detecting (a) Production of Monoclonal Antibodies Against Ribosome Protein L7/L12

*Escherichia coli* ribosomal protein L7/L12 monoclonal antibodies were used as the antibody to be labeled with gold colloids. Specifically, according to the method described in Example 5 of WO2000/006603 A, the L7/L12 ribosome protein of *Escherichia coli* was obtained and used for production of monoclonal antibodies. The monoclonal antibodies selected are a combination of two clones (EC-1 and EC-2) that can simultaneously bind to different sites of the L7/L12 ribosomal protein the above *Escherichia coli* and another *Escherichia* species.

(b) Gold Colloid Label-Impregnated Member

BB International gold colloid solution (60 nm particle size) in a volume of 0.9 mL was mixed with 0.1 M potassium phosphate pH 7.0, and then combined with 100 μg/mL of monoclonal antibody EC-2 to be labeled with gold colloids and allowed to stand for 10 minutes at room temperature, to allow this antibody to bind to the surface of the gold colloidal particles. A 10% aqueous solution of bovine serum albumin (BSA) was then added so that the final concentration in the gold colloid solution was 1% to block the remaining surface of the gold colloidal particles with BSA, whereby a solution of gold colloid-labeled monoclonal antibody EC-2 (hereafter referred to as the "gold colloid-labeled antibody") was prepared. This solution was centrifuged (at 15000×rpm for 5 minutes) to precipitate the gold colloid-labeled antibody, and the supernatant solution was removed to obtain the gold colloid-labeled antibody. This gold colloid-labeled antibody was then suspended in 20 mM tris hydrochloric acid buffer solution (pH 8.2) containing 0.25% BSA, 2.5% sucrose, and 35 mM NaCl to thereby obtain a gold colloid-labeled antibody solution. A strip of glass fiber pad of 10 mm×300 mm was impregnated with 2 mL of the gold colloid-labeled antibody solution and dried under reduced pressure at room temperature to prepare a gold colloid-labeled antibody-impregnated member (hereinafter referred to as gold colloid-labeled antibody-impregnated member 1) as the labeling antibody-attached member 1.

(c) Capture Site of Complex Between Antigen and Gold Colloid-Labeled Antibody

A nitrocellulose membrane with a width of 25 mm and a length of 300 mm was prepared as the membrane carrier for chromatographic development 2 of chromatographic media. A solution containing 1.5 mg/mL of monoclonal antibody EC-1 was applied in a line at 1 μL/cm at a position of 10 mm from the end of the chromatographic development start point on the membrane carrier for chromatographic development 2. The membrane carrier was dried at 50° C. for 30 minutes, then soaked in a 0.5% sucrose solution for 30 minutes, and dried at room temperature overnight, whereby the capture site 3 for the complex formed of the *Escherichia coli* ribosome protein L7/L12 antigen and the gold colloid-labeled antibody.

(d) Bacteriolysis Enzyme-Attached Member

Lysozyme manufactured by Creative Enzymes was dissolved in 20 mM tris hydrochloric acid buffer solution (pH 8.0) to a concentration of 50 mg/mL. A strip of glass fiber pad of 5 mm×300 mm was impregnated with 1 mL of the enzyme solution and air dried at room temperature to prepare a bacteriolysis enzyme-attached member 4.

(e) Production of an Immunochromatographic Device

A cross-sectional view of the immunochromatographic detection system is shown in FIG. 3.

In addition to the gold colloid-labeled antibody-impregnated member 1, the bacteriolysis enzyme-attached member 4, and the membrane carrier for chromatographic development 2 explained above, a sample contact member 5, a filter member 6, and an absorption member 7 were layered on a base material 8, and cut into 5 mm in width, to thereby produce an immunochromatographic detection device 30. The gold colloid-labeled antibody-impregnated member 1 was arranged on the upstream end side of the sample contact member 5, between the base material 8 and the sample contact member. The bacteriolysis enzyme-attached member 4 is arranged on the downstream side of the gold colloid-labeled antibody-impregnated member 1, between the base material 8 and the gold colloid-labeled antibody-impregnated member 1. A 23-mm GF/DVA (GE Healthcare Biosciences: filter member made of glass fiber with a thickness of 776 μm and a retained particle size of 3.5 μm) was used as the sample contact member 5. This member also serves as a member for removing fat globules. A 16-mm GF/AVA (GE Healthcare Biosciences: filter member made of glass fiber with a thickness of 299 μm and a retained particle size of 1.7 μm) was used as the filter member 6, filter paper was used as the absorbent member 7, and a 254-μm thick polystyrene film with adhesive material to attach other members was used as the base material 8.

(3) Production of an Immunochromatographic Detection Device for Detecting *Streptococcus* Species in Milk An immunochromatographic detection device was produced according to the following procedure.

(a) Production of Monoclonal Antibodies Against Ribosome Protein L7/L12

According to the method described in Example 5 of WO2000/06603 A, the L7/L12 ribosome protein of *Streptococcus uberis* was obtained and used for production of monoclonal antibodies. The monoclonal antibodies selected are a combination of two clones that can simultaneously bind to different sites of the L7/L12 ribosomal protein above.

(b) Gold Colloid Label-Impregnated Member

BB International gold colloid solution (60 nm particle size) in a volume of 0.9 mL was mixed with 0.1 M potassium phosphate pH 7.0, and then combined with 100 μg/mL of monoclonal antibody SU-2 to be labeled with gold colloids and allowed to stand for 10 minutes at room temperature, to allow this antibody to bind to the surface of the gold colloidal particles. A 10% aqueous solution of bovine serum albumin (BSA) was then added so that the final concentration in the gold colloid solution was 1% to block the remaining surface of the gold colloidal particles with BSA, whereby a solution of gold colloid-labeled monoclonal antibody SU-2 (hereafter referred to as the "gold colloid-labeled antibody") was prepared. This solution was centrifuged (at 15000×rpm for 5 minutes) to precipitate the gold colloid-labeled antibody, and the supernatant solution was removed to obtain the gold colloid-labeled antibody. This gold colloid-labeled antibody was then suspended in 20 mM tris hydrochloric acid buffer solution (pH 8.2) containing 0.25% BSA, 2.5% sucrose, and 35 mM NaCl to thereby obtain a gold colloid-labeled antibody solution. A strip of glass fiber pad of 10 mm×300 mm was impregnated with 2 mL of the gold colloid-labeled antibody solution and dried under reduced pressure at room temperature to prepare a gold colloid-labeled antibody-impregnated member (hereinafter referred to as gold colloid-labeled antibody-impregnated member 1) as the labeling antibody-attached member 1.

(c) Capture Site of Complex Between Antigen and Gold Colloid-Labeled Antibody

A nitrocellulose membrane with a width of 25 mm and a length of 300 mm was prepared as the membrane carrier for chromatographic development 2 of chromatographic media. A solution containing 1.5 mg/mL of monoclonal antibody SU-1 was applied in a line at 1 μL/cm at a position of 10 mm from the end of the chromatographic development start point on the membrane carrier for chromatographic development 2. The membrane carrier was dried at 50° C. for 30 minutes, then soaked in a 0.5% sucrose solution for 30 minutes, and dried at room temperature overnight, whereby the capture site 3 for the complex formed of the *Streptococcus uberis* ribosome protein L7/L12 antigen and the gold colloid-labeled antibody.

(d) Bacteriolysis Enzyme-Attached Members

Lysozyme manufactured by Creative Enzymes was dissolved in 20 mM tris hydrochloric acid buffer solution (pH 8.0) to a concentration of 50 mg/mL. A strip of glass fiber pad of 5 mm×300 mm was impregnated with 1 mL of the enzyme solution and air dried at room temperature to prepare a bacteriolysis enzyme-attached member 4-1.

Labiase manufactured by Cosmo Bio Co., Ltd. was dissolved in 20 mM tris hydrochloric acid buffer solution (pH 8.0) to a concentration of 30 μg/mL. A strip of glass fiber pad of 5 mm×300 mm was impregnated with 1 mL of the enzyme solution and air dried at room temperature to prepare a bacteriolysis enzyme-attached member 4-2.

(e) Production of an Immunochromatographic Device

A cross-sectional view of the immunochromatographic detection system is shown in FIG. 4.

In addition to the gold colloid-labeled antibody-impregnated member 1, the bacteriolysis enzyme-attached members 4-1 and 4-2, and the membrane carrier for chromatographic development 2 explained above, a sample contact member 5, a filter member 6, and an absorption member 7 were layered on a base material 8, and cut into 5 mm in width, to thereby produce an immunochromatographic detection device 40. The gold colloid-labeled antibody-impregnated member 1 was arranged on the upstream end of the sample contact member 5, between the base material 8 and the sample contact member 5. The bacteriolysis enzyme-attached member 4-1 and the bacteriolysis enzyme-attached member 4-2 were arranged on the downstream side of the gold colloid-labeled antibody-impregnated member 1, between the base material 8 and the gold colloid-labeled antibody-impregnated member 1. A 20-mm GF/DVA (GE Healthcare Biosciences: filter member made of glass fiber with a thickness of 776 μm and a retained particle size of 3.5 μm) was used as the sample contact member 5. This member also serves as a member for removing fat globules. A 16-mm GF/AVA (GE Healthcare Biosciences: filter member made of glass fiber with a thickness of 299 μm and a retained particle size of 1.7 μm) was used as the filter member 6, filter paper was used as the absorbent member 7, and a 254-μm thick polystyrene film with adhesive material to attach other members was used as the base material 8.

(4) Test Measurement of Milk with the Immunochromatographic Detection Devices

Figure 5:
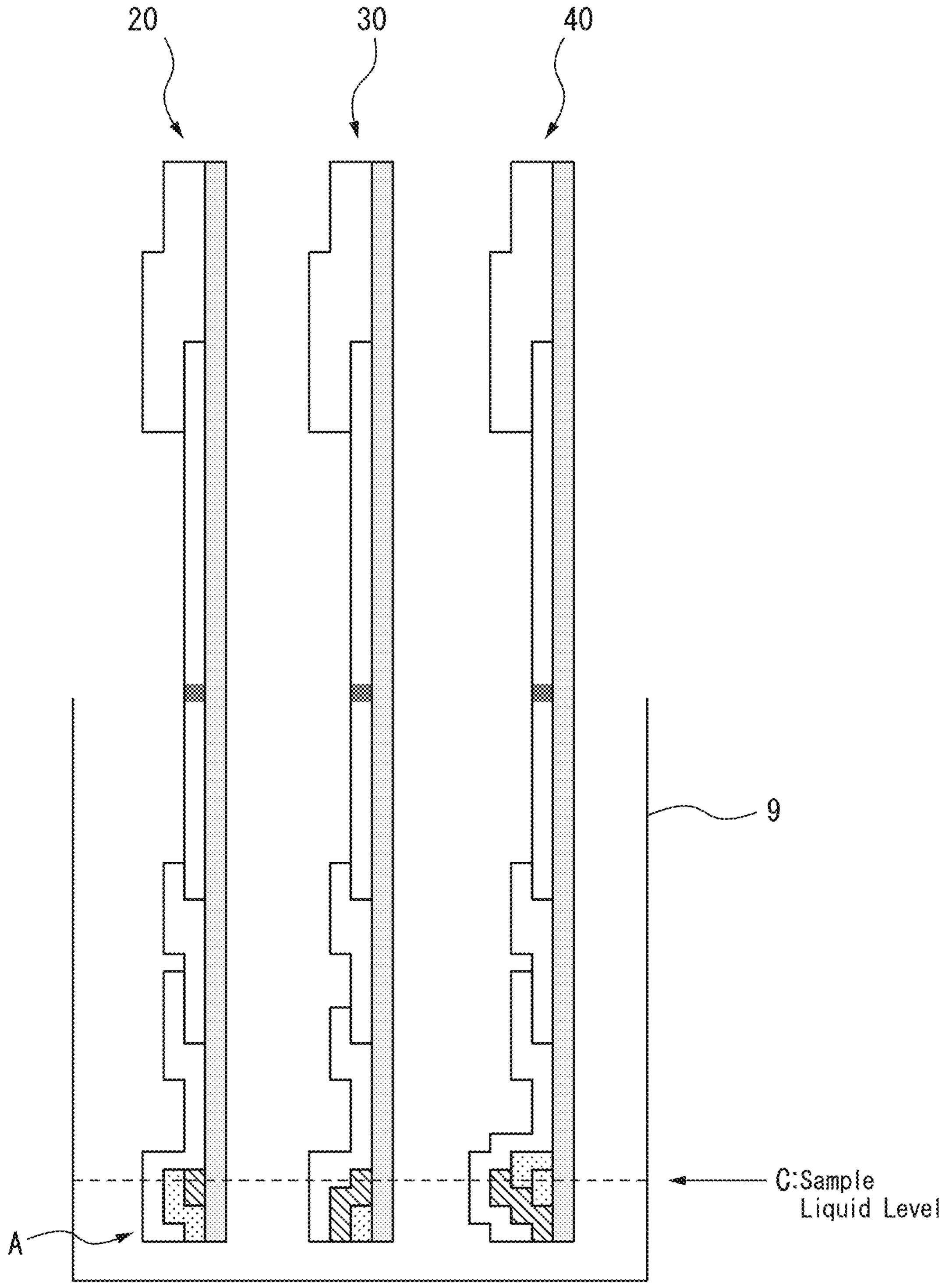
FIG. 5 is a schematic diagram showing the strip-shaped detection device described in any of FIGS. 2 to 4 being immersed in a mixture solution of the sample and the bacteriolysis aid. The dotted line represents the liquid level.

The measurement of milk using the immunochromatography detection devices 20, 30, and 40 was performed as follows: in each of cylindrical containers with an inner diameter of 17 mm, 900 μL of each bacteriolysis aid solution described in Condition 21 of Table 8 was dispensed, and 900 μL of a milk sample with *Staphylococcus aureus* and/or *Escherichia coli* and/or *Streptococcus uberis* at a final concentration of $1\times10^5$ (cfu/mL) was mixed under conditions described in Conditions 23 to 27 in Table 9. The pH and electrical conductivity of the bacteriolysis aid were measured using a compact pH meter LAQUA twin and a compact electrical conductivity meter LAQUAtwin (HORIBA), respectively. The milk used was a commercial product (pH 6.4, electrical conductivity 4.0 mS/cm). After measuring the pH and electrical conductivity of the mixture solution, portions of the sample contact members 5 of the immunochromatographic detection devices 20, 30, or 40 for detection of each bacterial species in milk were immersed as shown in FIG. 5, and the solution was agitated with the immunochromatographic detection devices, and allowed to stand at room temperature for 60 minutes to develop, and the reddish purple line was visually determined. The results are shown in Table 9.

TABLE 9

| | Bacterium added to Milk | | | Determination results by Kit | | |
|---|---|---|---|---|---|---|
| Condition | *Staphylococcus aureus* | *Escherichia coli* | *Streptococcus uberis* | *Staphylococcus aureus* | *Escherichia coli* | *Streptococcus uberis* |
| 23 | − | − | − | − | − | − |
| 24 | + | − | − | + | − | − |
| 25 | − | + | − | − | + | − |
| 26 | − | − | + | − | − | + |
| 27 | + | + | + | + | + | + |

It was shown that the use of the bacteriolysis aid of the present invention made it possible to detect *Staphylococcus aureus* and/or *Escherichia coli* and/or *Streptococcus uberis* in milk in the container in a single test.

Example 6: Simultaneous Detection of *Staphylococcus aureus, Escherichia Coli*, and *Streptococcus uberis* by Immunochromatography 2

(1) Production of an Immunochromatographic Detection Device for Simultaneously Detecting *Staphylococcus aureus, Escherichia Coli*, and *Streptococcus* Species An immunochromatographic detection device was produced according to the following procedure.

(a) Monoclonal Antibodies Against Ribosome Protein L7/L12 were Produced According to the Same Procedure as in Example 1(1)(*a*).

(b) Gold Colloid Label-Impregnated Member

BB International gold colloid solution (60 nm particle size) in a volume of 0.9 mL was mixed with 0.05M acetic acid buffer solution, pH 4.73, and then combined with 100 μg/mL of monoclonal antibody SA-2 to be labeled with gold colloids and allowed to stand for 30 minutes at room temperature, to allow this antibody to bind to the surface of the gold colloidal particles. 0.005% aqueous solution of SH-PEG5000 (PEG) was then added so that the final concentration in the gold colloid solution was 0.00024% and allowed to stand for 30 minutes to block the remaining surface of the gold colloidal particles with PEG. A 10% aqueous solution of bovine serum albumin (BSA) was then added so that the final concentration in the gold colloid solution was 0.87% to block the remaining surface of the gold colloidal particles with BSA. After centrifugation at 6500G for 20 minutes, the supernatant was removed, and the precipitate was re-dispersed in 20 mM tris hydrochloric acid buffer solution (pH 9.0) containing 0.5% BSA, 0.125% casein, 75 mM sodium chloride, and 0.1% sodium azide (hereinafter also referred to as "gold colloid dispersion medium"). Centrifugation was again performed under the same conditions, and the precipitate was diluted with the gold colloid dispersion medium so that the absorbance at 540 nm was 15, to thereby obtain a gold colloid-labeled antibody solution for *Staphylococcus aureus.*

BB International gold colloid solution (60 nm particle size) in a volume of 0.9 mL was mixed with 0.2M CAPSO buffer solution pH 9.3, and then combined with 100 μg/mL of monoclonal antibody EC-2 to be labeled with gold colloids and allowed to stand for 30 minutes at room temperature, to allow this antibody to bind to the surface of the gold colloidal particles. 0.005% aqueous solution of SH-PEG5000 (PEG) was then added so that the final concentration in the gold colloid solution was 0.00024% and allowed to stand for 60 minutes to block the remaining surface of the gold colloidal particles with PEG. A 2.5% aqueous solution of casein was then added so that the final concentration in the gold colloid solution was 0.217% to block the remaining surface of the gold colloidal particles with casein. After centrifugation at 6500G for 20 minutes, the supernatant was removed, and the precipitate was re-dispersed in the gold colloid dispersion medium so that the absorbance at 540 nm was 13.5, to thereby obtain a gold colloid-labeled antibody solution for *Escherichia coli.*

BB International gold colloid solution (60 nm particle size) in a volume of 0.9 mL was mixed with 0.1M TAPS buffer solution pH 7.75, and then combined with 100 μg/mL of monoclonal antibody EC-2 to be labeled with gold colloids and allowed to stand for 30 minutes at room temperature, to allow this antibody to bind to the surface of the gold colloidal particles. 0.005% aqueous solution of SH-PEG5000 (PEG) was then added so that the final concentration in the gold colloid solution was 0.00024% and allowed to stand for 15 minutes to block the remaining surface of the gold colloidal particles with PEG. A 5.0% aqueous solution of casein was then added so that the final concentration in the gold colloid solution was 0.434% to block the remaining surface of the gold colloidal particles with casein. After centrifugation at 6500G for 20 minutes, the supernatant was removed, and the precipitate was re-dispersed in the gold colloid dispersion medium so that the absorbance at 540 nm was 15.0, to thereby obtain a gold colloid-labeled antibody solution for *Streptococcus* species.

The gold colloid-labeled antibody solution for *Staphylococcus aureus*, the gold colloid-labeled antibody solution for *Escherichia coli*, and the gold colloid-labeled antibody solution for *Streptococcus* species were mixed in equal proportions. A 10 mm×300 mm strip of glass fiber pad was impregnated with 1.8 mL of the mixed antibody solution and dried at room temperature to prepare a gold colloid-labeled antibody-impregnated member (hereinafter referred to as the gold colloid-labeled antibody-impregnated member 1) as the labeling antibody-attached member 1.

(c) Capture Site of Complex Between Antigen and Gold Colloid-Labeled Antibody

A nitrocellulose membrane with a width of 25 mm and a length of 300 mm was prepared as the membrane carrier for chromatographic development 2 (second part) of chromatographic media. A 3.0 mg/mL monoclonal antibody SA-1 solution containing 0.15% casein and 1% sucrose, a 1.0 mg/mL monoclonal antibody EC-1 solution containing 0.10% casein and 2% sucrose, and a 2.5 mg/mL monoclonal antibody SU-1 solution containing 0.1% casein and 0.5% sucrose were applied each in a line with a concentration of 0.571 μL/cm at 5, 6.5, and 8 mm, respectively, from the end of the chromatographic development start point side in the membrane carrier for chromatographic development 2. The membrane carrier was dried at 60° C. for 30 minutes, whereby the capture site 3 for the complex formed of the ribosome protein L7/L12 antigens of each of *Staphylococcus aureus, Escherichia coli*, and *Streptococcus uberis* and the corresponding gold colloid-labeled antibody.

(d) Bacteriolysis Enzyme-Attached Member

Recombinant lysostaphin manufactured by Fujifilm Wako Pure Chemical Corporation and lysozyme manufactured by Creative Enzymes were dissolved in 20 mM sodium acetate buffer (pH 4.5) containing 5% sucrose to concentration of 0.133 g/mL and 133 g/mL, respectively. A strip of glass fiber pad of 5 mm×300 mm was impregnated with 0.9 mL of the enzyme solution and air dried at room temperature to prepare a bacteriolysis enzyme-attached member 4-1.

Labiase manufactured by Cosmo Bio Co., Ltd. was dissolved in McIlvaine buffer (pH 4.0) containing 5% sucrose to a concentration of 30 μg/mL. A strip of glass fiber pad of 5 mm×300 mm was impregnated with 0.9 mL of the enzyme solution and air dried at room temperature to prepare a bacteriolysis enzyme-attached member 4-2.

(e) Production of an Immunochromatographic Device

Figure 6:
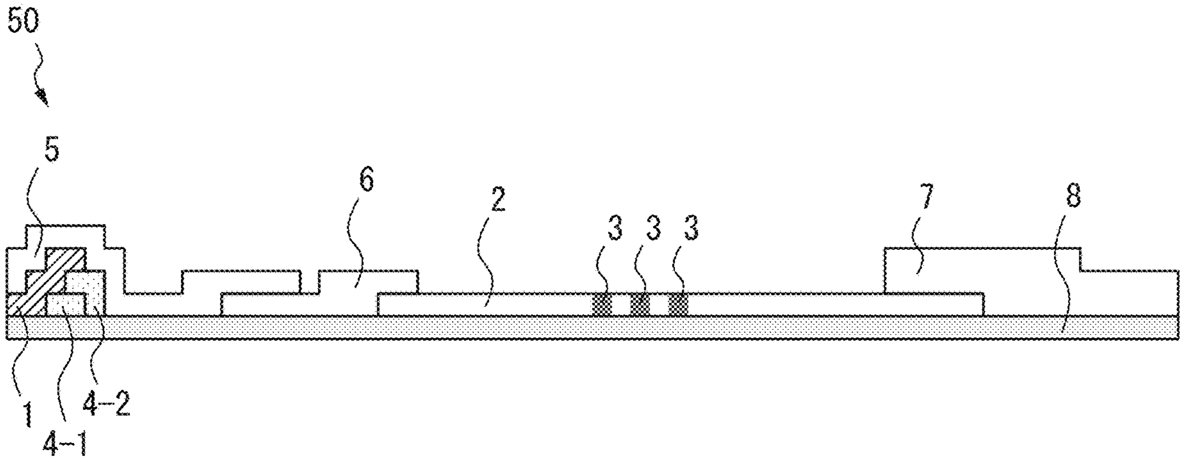
FIG. 6 is a cross-sectional view of a schematic diagram of a strip-shaped detection mechanism as an example of a detection mechanism of a lateral flow type immunochromatographic detection system for detecting *Staphylococcus aureus, Escherichia* species, and *Streptococcus* species simultaneously.

A cross-sectional view of the immunochromatographic detection system is shown in FIG. 6.

In addition to the gold colloid-labeled antibody-impregnated member 1, the bacteriolysis enzyme-attached members 4-1 and 4-2, and the membrane carrier for chromatographic development 2 explained above, a sample contact member 5, a filter member 6, and an absorption member 7 were layered on a base material 8, and cut into 5 mm in width, to thereby produce an immunochromatographic detection device 40. The gold colloid-labeled antibody-impregnated member 1 was arranged on the upstream end of the sample contact member 5, between the base material 8 and the sample contact member 5. The bacteriolysis enzyme-attached member 4-1 and the bacteriolysis enzyme-attached member 4-2 were arranged on the downstream side of the gold colloid-labeled antibody-impregnated member 1, between the base material 8 and the gold colloid-labeled antibody-impregnated member 1. A 20-mm GF/DVA (GE Healthcare Biosciences: filter member made of glass fiber with a thickness of 776 μm and a retained particle size of 3.5 μm) was used as the sample contact member 5. This member also serves as a member for removing fat globules. A 16-mm GF/AVA (GE Healthcare Biosciences: filter member made of glass fiber with a thickness of 299 μm and a retained particle size of 1.7 μm) was used as the filter member 6, filter paper was used as the absorbent member 7, and a 254-μm thick polystyrene film with adhesive material to attach other members was used as the base material 8.

(2) Test Measurement of Milk with the Immunochromatographic Detection Devices

Figure 7:
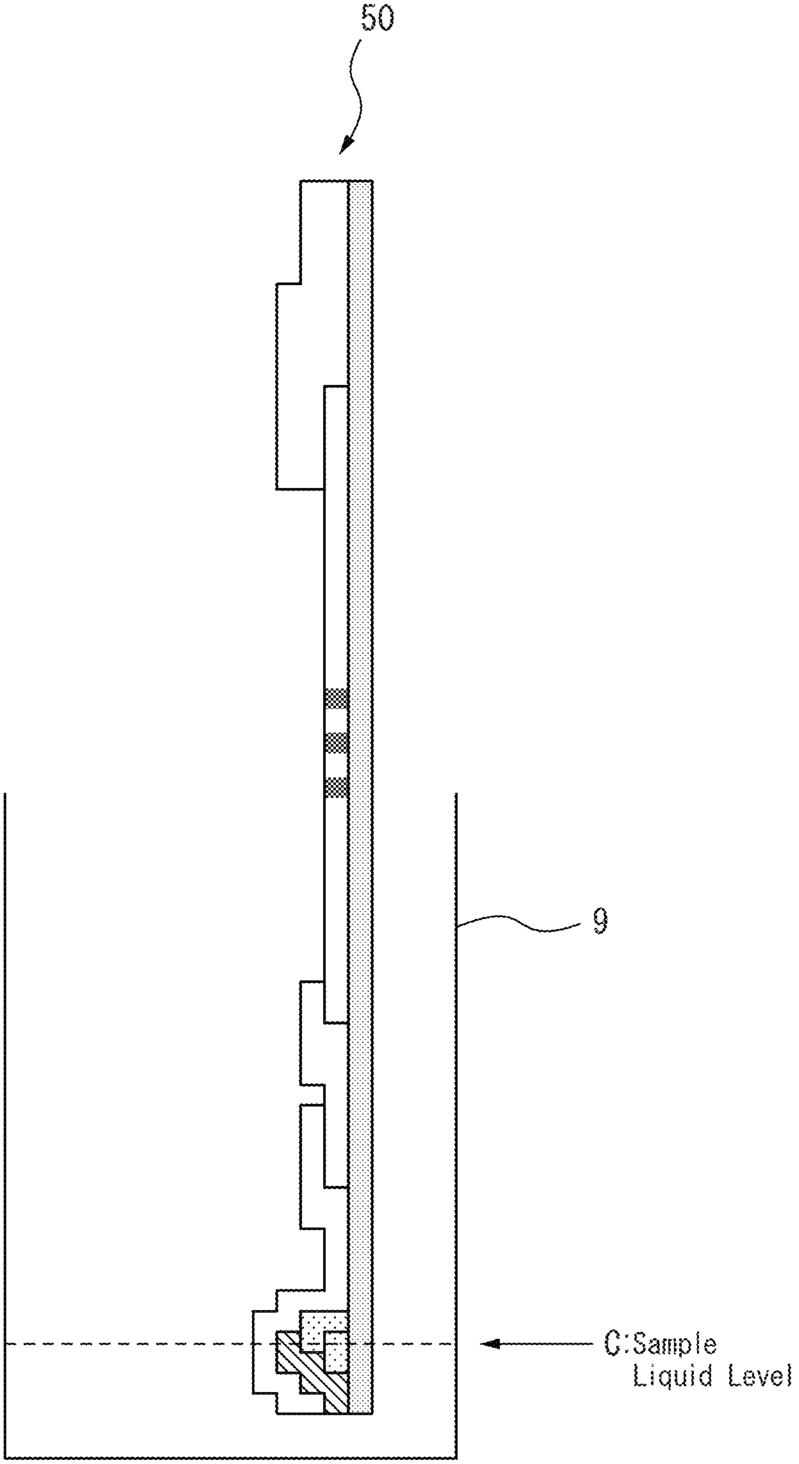
FIG. 7 is a schematic diagram showing the lateral flow type immunochromatographic detection device for detecting *Staphylococcus aureus, Escherichia* species, and *Streptococcus* species simultaneously being immersed in a mixture solution of the sample and the bacteriolysis aid. The dotted line represents the liquid level.

The measurement of milk using the immunochromatography detection devices 20, 30, and 40 was performed as follows: in each of cylindrical containers with an inner diameter of 17 mm, 300 μL of each bacteriolysis aid solution described in Condition 21 of Table 8 was dispensed, and 300 μL of a milk sample with *Staphylococcus aureus* and/or *Escherichia coli* and/or *Streptococcus uberis* at a final concentration of $1\times10^5$ (cfu/mL) was mixed under conditions described in Conditions 23 to 27 in Table 9. The pH and electrical conductivity of the bacteriolysis aid were measured using a compact pH meter LAQUA twin and a compact electrical conductivity meter LAQUAtwin (HORIBA), respectively. The milk used was a commercial product (pH 6.4, electrical conductivity 4.0 mS/cm). After measuring the pH and electrical conductivity of the mixture solution, a portion of the sample contact member 5 of immunochromatographic detection device for simultaneously detecting *Staphylococcus aureus, Escherichia coli*, and *Streptococcus uberis* in milk were immersed as shown in FIG. 7, and the solution was agitated with the immunochromatographic detection device for simultaneously detecting *Staphylococcus aureus, Escherichia coli*, and *Streptococcus uberis*, and allowed to stand at room temperature for 60 minutes to develop, and the reddish purple line was visually determined. The results are shown in Table 10.

TABLE 10

| Condition | Bacterium added to Milk: *Staphylococcus aureus* | Bacterium added to Milk: *Escherichia coli* | Bacterium added to Milk: *Streptococcus uberis* | Determination results by Kit: *Staphylococcus aureus* | Determination results by Kit: *Escherichia coli* | Determination results by Kit: *Streptococcus uberis* |
|---|---|---|---|---|---|---|
| 42 | − | − | − | − | − | − |
| 43 | + | − | − | + | − | − |
| 44 | − | + | − | − | + | − |
| 45 | − | − | + | − | − | + |
| 46 | + | + | + | + | + | + |

INDUSTRIAL APPLICABILITY

The present invention is widely applicable to the fields of food, livestock breeding, etc., including bacteriolysis and bacterial detection, and its use is therefore extremely valuable.

EXPLANATION OF SYMBOLS

10: Immunochromatographic detection device
20: Immunochromatographic device for detection of *Staphylococcus aureus*
30: Immunochromatographic device for detection of *Escherichia coli*
40: Immunochromatographic device for detection of *Streptococcus uberis*
50: Immunochromatographic device for detection of three species
1: Labeling antibody-attached member (conjugate pad)/Gold colloid-labeled antibody-impregnated member
2: Membrane carrier for chromatographic development
3: Capture site
4: Bacteriolysis enzyme-attached member
4-1: Bacteriolysis enzyme-attached member
4-2: Bacteriolysis enzyme-attached member
5: Sample contact member (sample pad)
6: Filter member
7: Absorption member (absorption pad)
8: Base material
9: Container
A: Sample
B: Sample flow
C: Sample fluid level

The invention claimed is:

1. A method for lysing a group of bacteria in the sample, comprising the step of lysing the group of bacteria in the sample in a mixture solution obtained by mixing the sample, a bacteriolysis enzyme, and a bacteriolysis aid, wherein the bacteriolysis enzyme includes at least one bacteriolysis enzyme selected from the group consisting of lysostaphin, lysozyme, acetyl glucosaminidase, and endopeptidase, and wherein the mixture solution has a pH of from 6.0 to 7.0 and an electrical conductivity of from 2.5 to 8.5 mS/cm.

2. The method according to claim 1, wherein the bacteriolysis enzyme and the bacteriolysis aid are pre-mixed.

3. The method according to claim 1, wherein the bacteriolysis aid contains a buffer and a surfactant.

4. The method according to claim 3, wherein the bacteriolysis aid further contains a salt.

5. The method according to claim 3, wherein the surfactant contains at least nonionic surfactant.

6. The method according to claim 5, wherein the nonionic surfactant includes a first nonionic surfactant having a polyoxyethylene chain, wherein the polyoxyethylene chain has an average number of repeats of from 7 to 11 and a Hydrophilic-Lipophilic Balance (HLB) value of 12.0 or more less than 14.5.

7. The method according to claim 6, wherein the polyoxyethylene chain has an average number of repeats of from 7.5 to 10 and an HLB value of 12.4 to 14.1.

8. The method according to claim 6, wherein the concentration of the first nonionic surfactant in the mixture solution is from 1.25 to 3.125%.

9. The method according to claim 5, wherein the bacteriolysis aid contains 5 to 500 mM buffer.

10. The method according to claim 1, wherein the bacteriolysis enzyme include all four bacteriolysis enzymes selected from the group consisting of lysostaphin, lysozyme, acetyl glucosaminidase, and endopeptidase.

11. The method according to claim 1, wherein the bacteriolysis subject of the method includes at least one bacterial species selected from the group consisting of *Escherichia* species, *Staphylococcus* species, and *Streptococcus* species.

12. The method according to claim 10, wherein the bacteriolysis subject of the method includes *Escherichia* species, *Staphylococcus* species, and *Streptococcus* species.

13. The method according to claim 1, wherein the method is carried out as a pretreatment for L7/L12 ribosome protein antigen detection.

14. The method according to claim 1, wherein the sample is milk.

15. A method for lysing a group of bacteria in a sample, comprising the step of mixing the sample, a bacteriolysis enzyme, and a bacteriolysis aid, wherein the bacteriolysis enzyme includes at least one bacteriolysis enzyme selected from the group consisting of lysostaphin, lysozyme, acetyl glucosaminidase, and endopeptidase, and wherein the bacteriolysis aid has a pH of from 6.0 to 7.0 and an electrical conductivity of from 2.0 to 8.0 mS/cm.

16. The method according to claim 15, wherein the bacteriolysis enzyme and the bacteriolysis aid are provided as a pre-mixed state.

17. The method according to claim 15, wherein the bacteriolysis aid contains a buffer and a surfactant.

18. The method according to claim 17, wherein the bacteriolysis aid further contains a salt.

19. The method according to claim 17, wherein the surfactant contains at least nonionic surfactant.

20. The method according to claim 19, wherein the nonionic surfactant includes a first nonionic surfactant having a polyoxyethylene chain, wherein the polyoxyethylene chain has an average number of repeats of from 7 to 11 and an HLB value of 12.0 or more less than 14.5.

21. The method according to claim 20, wherein the polyoxyethylene chain has an average number of repeats of from 7.5 to 10 and an HLB value of 12.4 to 14.1.

22. The method according to claim 19, wherein the concentration of the nonionic surfactant in the bacteriolysis aid is from 2 to 5%.

23. The method according to claim 17, wherein the bacteriolysis aid contains 5 to 500 mM buffer.

24. The method according to claim 15, wherein the bacteriolysis enzyme include all four bacteriolysis enzymes selected from the group consisting of lysostaphin, lysozyme, acetyl glucosaminidase, and endopeptidase.

25. The method according to claim 15, wherein the bacteriolysis subject of the method includes at least one bacterial species selected from the group consisting of *Escherichia* species, *Staphylococcus* species, and *Streptococcus* species.

26. The method according to claim 24, wherein the bacteriolysis subject of the method includes *Escherichia* species, *Staphylococcus* species, and *Streptococcus* species.

27. The method according to claim 15, wherein the method is carried out as a pretreatment for L7/L12 ribosome protein antigen detection.

28. The method according to claim 15, wherein the sample is milk.

29. The method according to claim 15, wherein the sample and the bacteriolysis aid are mixed at a ratio of from 1:5 to 3:1.

30. A bacteriolysis aid comprising 0 to 1.5 M of salts, 5 to 500 mM of a buffer, and 2 to 5% of a nonionic surfactant, and having a pH of from 6.0 to 7.0 and an electrical conductivity of from 2.0 to 8.0 mS/cm, in a sample in combination with at least one bacteriolysis enzyme selected from the group consisting of lysostaphin, lysozyme, acetyl glucosaminidase, and endopeptidase for lysing a group of bacteria including *Escherichia* species, *Staphylococcus* species, and *Streptococcus* species.

31. A bacteriolysis kit comprising at least one bacteriolysis enzyme selected from the group consisting of lysostaphin, lysozyme, acetyl glucosaminidase, and endopeptidase and the bacteriolysis aid according to claim 30.

32. A bacterial detection kit comprising at least one bacteriolysis enzyme selected from the group consisting of lysostaphin, lysozyme, acetyl glucosaminidase, and endopeptidase, the bacteriolysis aid according to claim 30, and a device for detecting a L7/L12 ribosome protein antigen.

33. A method for determining the presence or absence of at least one species of bacteria selected from the group consisting of *Escherichia* species, *Staphylococcus* species, and *Streptococcus* species, and *Streptococcus* species, in a sample, comprising the steps of:

mixing the sample, a bacteriolysis enzyme, and a bacteriolysis aid to prepare a mixture solution; and determining the presence or absence of the bacteria by detecting a L7/L12 ribosome protein derived from the bacteria contained in the mixture solution by means of an immunological method, wherein the bacteriolysis enzyme includes at least one bacteriolysis enzyme selected from the group consisting of lysostaphin, lysozyme, acetyl glucosaminidase, and endopeptidase, wherein the mixture solution has a pH of from 6.0 to 7.0 and an electrical conductivity of from 2.5 to 8.5 mS/cm, wherein in the step to prepare the mixture solution, the lysozyme can lyse the *Escherichia* species, the lysostaphin can lyse the *Staphylococcus* species, and the lysozyme, acetyl glucosaminidase, and endopeptidase can lyse the *Streptococcus* species.

34. The method according to claim 33, wherein the bacteriolysis aid contains a buffer and a surfactant.

35. The method according to claim 34, wherein the surfactant contains at least nonionic surfactant.

36. The method according to claim 35, wherein the nonionic surfactant includes a first nonionic surfactant having a polyoxyethylene chain, wherein the polyoxyethylene chain has an average number of repeats of from 7 to 11 and an HLB value of 12.0 or more less than 14.5.

37. The method according to claim 36, wherein the polyoxyethylene chain has an average number of repeats of from 7.5 to 10 and an HLB value of 12.4 to 14.1.

38. The method according to claim 36, wherein the concentration of the first nonionic surfactant in the mixture solution is from 1.25 to 3.125%.

39. The method according to claim 33, wherein the bacteriolysis enzyme include all four bacteriolysis enzymes selected from the group consisting of lysostaphin, lysozyme, acetyl glucosaminidase, and endopeptidase.

* * * * *